(12) United States Patent
Yamada et al.

(10) Patent No.: US 10,288,604 B2
(45) Date of Patent: May 14, 2019

(54) METHOD FOR IMAGING CELL USING FLUORESCENCE-LABELED SUGAR DERIVATIVE HAVING COUMARIN DERIVATIVE BOUND THERETO, AND IMAGING AGENT

(71) Applicant: HIROSAKI UNIVERSITY, Hirosaki-shi, Aomori (JP)

(72) Inventors: Katsuya Yamada, Hirosaki (JP); Tadashi Teshima, Minoh (JP); Toshihiro Yamamoto, Ibaraki (JP)

(73) Assignee: HIROSAKI UNIVERSITY, Hirosaki-shi, Aomori (JP)

( * ) Notice: Subject to any disclaimer, the term of this patent is extended or adjusted under 35 U.S.C. 154(b) by 262 days.

(21) Appl. No.: 14/431,523

(22) PCT Filed: Oct. 1, 2013

(86) PCT No.: PCT/JP2013/076629
§ 371 (c)(1),
(2) Date: Jul. 29, 2015

(87) PCT Pub. No.: WO2014/054601
PCT Pub. Date: Apr. 10, 2014

(65) Prior Publication Data
US 2015/0369797 A1 Dec. 24, 2015

(30) Foreign Application Priority Data

Oct. 3, 2012 (JP) ................................. 2012-221049

(51) Int. Cl.
| G01N 33/50 | (2006.01) |
| A61K 49/00 | (2006.01) |
| G01N 33/533 | (2006.01) |
| G01N 33/574 | (2006.01) |
| G01N 33/58 | (2006.01) |
| C07H 13/10 | (2006.01) |
| C07H 3/02 | (2006.01) |

(52) U.S. Cl.
CPC ..... *G01N 33/5091* (2013.01); *A61K 49/0039* (2013.01); *A61K 49/0052* (2013.01); *C07H 3/02* (2013.01); *C07H 13/10* (2013.01); *G01N 33/533* (2013.01); *G01N 33/574* (2013.01); *G01N 33/582* (2013.01); *G01N 2400/00* (2013.01); *G01N 2800/7028* (2013.01)

(58) Field of Classification Search
CPC .................................................. A61K 49/0039
See application file for complete search history.

(56) References Cited

U.S. PATENT DOCUMENTS

| 5,830,912 | A | 11/1998 | Gee et al. |
| 5,877,310 | A | 3/1999 | Reddington et al. |
| 6,989,140 | B2 | 1/2006 | Tidmarsh et al. |
| 8,986,656 | B2 | 3/2015 | Yamada et al. |
| 2007/0031898 | A1 | 2/2007 | Suga et al. |
| 2011/0189708 | A1 | 8/2011 | Yamada et al. |
| 2011/0312012 | A1* | 12/2011 | Skinderso ............... C09B 15/00 435/29 |
| 2013/0183700 | A1 | 7/2013 | Drevelle et al. |
| 2014/0154717 | A1* | 6/2014 | Yamada ............. A61K 49/0054 435/14 |

FOREIGN PATENT DOCUMENTS

| EP | 0867722 A2 | 9/1998 |
| JP | 7-20131 A | 1/1995 |
| JP | 10-267931 A | 10/1998 |
| JP | 2001-524969 A | 12/2001 |
| JP | 2009-190993 A | 8/2009 |
| JP | 2011-153096 A | 8/2011 |
| WO | 03059149 A2 | 7/2003 |
| WO | 2005108979 A1 | 11/2005 |
| WO | 2010016587 A1 | 2/2010 |
| WO | 2010027108 A1 | 3/2010 |
| WO | 2011098610 A1 | 8/2011 |
| WO | 2012038614 A1 | 3/2012 |
| WO | 2012070024 A1 | 5/2012 |
| WO | WO 2012/133688 A1 * | 10/2012 |

OTHER PUBLICATIONS

Sun et al. Bioorg. Med. Chem. Let. (1989) 8: 3107-3110.*
Higai et al. Biol. Pharm. bull. (1999) 2294): 333-338.*
Fukuda, H. et al., Eur. J. Nucl. Med. 11: 444-448, 1986.
Ishiwata, K et. al. Int J Rad Appl Instrum.B 16 : 247-254 1989.
Wuest, M., et al., Nuc.. Med. Biol. 38: 461-475, 2011.
Ido, T. et al., J. Labelled Compounds and Radiopharmaceuticals 14: 175-183, 1978.
Fukuda, H. et al., Eur. J. Nucl. Med. 7: 294-297, 1982.
Yamada K. et al., J. Biol. Chem. 275:22278-22283, 2000.
Yamada K. et al., Nat. Protoc. 2:753-762, 2007.
Levi, J. et al., Bioconjug. Chem. 18: 628-634 (2007).
O'Neil, R.G. et al, Mol. Imaging Biol. 7:388-392, 2005.
Sheth, R. et al, J. Biomed. Opt.14:064014-1-8, 2009.

(Continued)

*Primary Examiner* — Bin Shen
(74) *Attorney, Agent, or Firm* — Kratz, Quintos & Hanson, LLP

(57) ABSTRACT

The present invention has an object of providing a sugar derivative emitting blue fluorescence color which can be used for imaging of cells or intracellular molecules and a method for imaging cells using the derivative. Further, the present invention has an object of providing a method for detecting cancer cells at high accuracy by imaging, and an imaging agent used for this method. The present invention provides a fluorescently labeled sugar derivative having 3-carboxy-6,8-difluoro-7-hydroxycoumarin or 3-carboxymethyl-6,8-difluoro-7-hydroxy-4-methylcoumarin as a fluorescent molecular group in its molecule, and a cell imaging agent and an imaging method using the derivative. Further, the present invention provides an imaging agent and an imaging method for cancer cells using an L-glucose derivative having the above-described fluorescent molecular group in its molecule.

10 Claims, 10 Drawing Sheets

(56) References Cited

OTHER PUBLICATIONS

Nitin, N. et al, Int. J. Cancer 124; 2634-2642 (2009).
Cheng, Z. et al. Bioconjugate Chem. 17: 662-669, 2006.
Tian Y.S. et al., Angew Chem Int Ed. 48: 8027-8031, 2009.
Kovar JL, et al, Anal. Biochem. 384:254-262, 2009.
Supuran, C.T., Nat. Rev. Drug Discov. 7: 168-181 (2008).
Maresca, A. and Supuran, C.T., Bioorg. Med. Chem. Lett. 20: 4511-4514 (2010).
Supuran, C.T., World J. Clin. Oncol. 3: 98-103 (2012).
Kovar, JL et al, Anal., Biochem. 367; 1-12, 2007.
Bristow, R.G., and Hill, R.P. Nat. Rev. Cancer 8: 180-192, 2008.
Denko N.C. Nat. Rev. Cancer 8: 705-713, 2008.
Neri, D., et al. Nat. Rev. Drug Discov. 10: 767-777 (2011).
Wassennar W, et al., Cancer Res. 35, 785-790 (1975).
International Search Report dated Nov. 26, 2013 for PCT/JP2013/076629.
International Preliminary Report on Patentability dated Nov. 26, 2013 for PCT/JP2013/076629.
Supplementary European Search Report for corresponding European Application No. 13843405.5 dated Apr. 1, 2016.
Nitin Nitin et al., "Molecular imaging of glucose uptake in oral neoplasia following topical application of flourescently labeled deoxy-glucose", International Journal of Cancer, vol. 124, No. 11, (Jun. 1, 2009), pp. 2634-2642.
Jelena Levi et al., "Fluorescent Fructose Derivatives for Imaging Breast Cancer Cells", Bioconjugate Chemistry, vol. 18, No. 3 (Aug. 18, 2007), pp. 628-634.
Meng, Jean, et al., "Synthesis of 2-[18F]Fluro-2-Deoxy-L-Glucose and Positron Emission Tomography Studies in Monkeys," Nucl. Med. Biol., vol. 21, No. 4, pp. 633-640, 1994.

\* cited by examiner

Nuclear staining by DAPI    Apoptotic cells (Annexin VII)    Necrotic (PI)

DIC image    Overlay

Images before administration of 2-NBDLG+2-TRLG+2-PBLG

Images during administration of 2-NBDLG+2-TRLG+2-PBLG

Images 2 min after completion of administration of 2-NBDLG+2-TRLG+2-PBLG

Images 8 min after completion of administration of 2-NBDLG+2-TRLG+2-PBLG

Images 12 min after completion of administration of 2-NBDLG+2-TRLG+2-PBLG

Enlarged images around the center after completion of administration of 2-NBDLG+2-TRLG+2-PBLG Images before administration of 2-TRLG+2-PBLG Images 2 min after completion of administration of 2-TRLG+2-PBLG Images 8 min after completion of administration of 2-TRLG+2-PBLG

METHOD FOR IMAGING CELL USING FLUORESCENCE-LABELED SUGAR DERIVATIVE HAVING COUMARIN DERIVATIVE BOUND THERETO, AND IMAGING AGENT

TECHNICAL FIELD

The present invention relates to a novel fluorescently labeled sugar derivative to which a specific coumarin derivative has been linked, and to a cell imaging method and an imaging agent using the same. Further, the present invention relates to a method for detecting and/or imaging cancer cells using an L-glucose derivative (specific coumarin derivative-linked L-glucose derivative) among the fluorescently labeled derivatives, and to an imaging agent used for this.

BACKGROUND ART

There is active implementation of molecular imaging in which living cells are targeted and visualized and imaged or imaging is performed to visualize targeted molecules in a living body, thereby clarifying molecular kinetics, intermolecular interaction and molecular position information, intending leading to elucidation of mechanism of life science and screening of new drugs. In particular, there are also active studies for detecting cancer cells and cancer lesions by visualizing abnormal cells, for example, cancer cells.

Most of six-carbon sugars (hexose) represented by glucose (grape sugar), for example, glucose, fructose, galactose and mannose play a critical role in activity of living organisms. Especially, glucose is known as the most important energy source for supporting cell lives in living things from mammals to *Escherichia coli* and yeast, and in particular, brain uses glucose as the sole energy source. Glucose includes mirror isomers: D-glucose and L-glucose, and only D-glucose among them can be utilized as an energy source by living organisms, and a living cell has a mechanism for taking up D-glucose selectively via transporter proteins in plasma membrane, such as glucose transporters and the like, and utilizing in the cell.

The six-carbon sugar (hexose), of which D-form occurs abundantly in nature and L-form as its optical isomer does not, or scarcely occurs, includes D-galactose, D-fructose and D-mannose in addition to glucose.

D-galactose is a sugar utilized as an energy source, contained abundantly in milk, fruits and vegetables, and additionally, produced at a rate of about 2 g per day also in a human body. For example, disaccharide lactose occupying 2 to 8% of milk is formed by D-galactose and D-glucose via glycoside linkage, and it is known that both the constituents are separated by lactase in absorption into small intestine, and absorbed into a body via SGLT a sort of glucose transporter. When D-galactose is transported from small intestinal epithelial cells into blood vessels, it passes through a glucose transporter GLUT2. Galactose taken up into cells undergoes phosphorylation at 1-position, then, enters the glycolytic pathway and is utilized as energy, or utilized for biosynthesis of glycolipid and glycoprotein. On the other hand, L-galactose is described as an intermediate metabolite in the Smirnoff-Wheeler pathway which is one of pathways when an antioxidant substance vitamin C (L-ascorbic acid) which cannot be biosynthesized by primates is biosynthesized from D-glucose in a plant, but is a rare sugar which is not usually seen in biology in general.

2-deoxy-2[$^{18}$F]fluoro-D-galactose obtained by labeling D-galactose with $^{18}$F has an example of application for analyzing metabolites in liver (non-patent document 1). 2-deoxy-2[$^{18}$F]fluoro-D-galactose has been reported to have a possibility of utilization for imaging of galactose metabolism in cancer, it has not been generalized, though (non-patent document 2).

D-fructose is also called fruit sugar, and is contained in large amounts in berries and fruits such as melon and the like and some kinds of root vegetables, produced also in the body, in addition. Ingested D-fructose is taken up into epithelial cells via a glucose transporter GLUT5 in small intestinal epithelium, then, enters mainly through GLUT2 into blood. Fructose, which has entered into hepatic cells, undergoes phosphorylation by fructokinase, and is used for synthesis of fatty acids and energy production, and in addition, converted also into D-glucose. Since GLUT5 is expressed also in smooth muscle, kidney, adipocyte, brain and testis, it is thought that GLUT5 plays important functions in these regions respectively, and for example, D-fructose is used as an energy source in sperm motility as well. Among the corn syrup that is widely circulated as a food sweetener, those having increased content of D-fructose, which is cheap and shows intense sweetness particularly at low temperatures, are used in large amounts in refreshing beverages and the like, and excessive intake of D-fructose exerts a bad influence on neuronal activity in brain and is considered dangerous as a trigger of obesity and cancers. There is a paper reporting that L-fructose can be utilized to some extent when eaten, but it has been also speculated that this may be due to a conversion by enterobacteria.

1-deoxy-1-[$^{18}$F]fluoro-D-fructose has been synthesized as a radiolabeled compound and moderate uptake thereof into tumor has been reported, however, this molecule appears to undergo no metabolism in a cell, and therefore, is not used. Recently, 6-deoxy-6-[$^{18}$F]fluoro-D-fructose, which is metabolized intracellularly, has been synthesized and reported as a candidate tracer for PET targeting uptake thereof via GLUT5 in breast cancer (non-patent document 3).

D-mannose is contained in fruits and fruit peel and the like. A polysaccharide composed mainly of mannose is called mannan, and contained in plants, yeasts and bacteria. Konjac contains as the main component glucomannan composed of mannose and glucose. D-mannose is, when orally taken in case of human, believed to be mostly excreted into urine in the usual case, and the way of uptake thereof in a human body is unclear in many aspects. When taken into a cell, D-mannose is phosphorylated, then, converted into fructose 6-phosphate, which is an intermediate in the glycolytic pathway.

A mannose receptor to which D-mannose binds specifically is helpful for eliminating high mannose glycoprotein, which increases during inflammation. For example, there is a high mannose sugar chain region on the membrane surface of *P. carini*, which is a causative microorganism of *carinii* pneumonia, a kind of opportunistic infection occupying the first cause of AIDS patients' death, and a mannose receptor occurring on alveolar macrophage recognizes this, thereby promoting migration of macrophage. Not only D-mannose but also L-galactose has a strong macrophage stimulating action, and additionally, both D-mannose and L-galactose are used as a precursor for biosynthesis of vitamin C in plants.

Though it is reported that [$^{18}$F]-2-fluoro-2-deoxy-D-mannose can be used as a cancer tracer, but this is not popularized (non-patent document 4, non-patent document 5).

As described above, various hexoses such as represented by glucose play an important role in living organisms.

However, all studies to examine the relationship between these hexoses and cells have a common issue as described below taking D-glucose as a typical example.

Conventionally, studies on how living organisms take up D-glucose into cells and utilize it have been conducted, for example, by measuring the intracellular quantity of a radio isotope using D-glucose labeled with the radio isotope or its derivatives (D-deoxyglucose or the like). This method is excellent for quantification, however, has a problem of low sensitivity, and in addition, it has a defect that D-glucose uptake into living cells cannot be observed continuously in real time due to the methodology of measurement. Then, the group of the present inventors has proposed a method of using green fluorescence emitting 2-[N-(7-nitrobenz-2-oxa-1,3-diazol-4-yl)amino]-2-deoxy-D-glucose (2-NBDG) obtained by linking an N-(7-nitrobenz-2-oxa-1,3-diazol-4-yl)amino group as a fluorescent chromophore at the 2-position of D-deoxyglucose, as a method which can be used in a study of the dynamic process of D-glucose uptake into living cells, and has demonstrated its usefulness using various cells of mammals (non-patent document 6).

This method uses a property of 2-NBDG which is selectively taken up into living cells, and since the dynamic activity of D-glucose uptake into a cell can be observed in a quantitative manner by tracing the change in the fluorescence intensity due to the uptake, this method is evaluated by researchers around the world as a ground-breaking method for studying how a living organism takes up D-glucose into a cell and utilizes it, and now, regarded as a standard protocol essential in this study field (non-patent document 7). Further, for evaluating specific uptake of D-glucose, the group of the present inventors has developed green fluorescence emitting 2-[N-(7-nitrobenz-2-oxa-1,3-diazol-4-yl)amino]-2-deoxy-L-glucose (2-NBDLG) obtained by linking an N-(7-nitrobenz-2-oxa-1,3-diazol-4-yl)amino group as a fluorescent chromophore at the 2-position of L-deoxyglucose, the enantiomer of D-deoxyglucose, and has also developed a L-deoxyglucose which is a glucose derivative emitting red fluorescence color (2-TRLG) in which sulforhodamine 101 is bound at its 2-position via sulfonamide-linking (patent document 1).

Further, there is a report of application of a molecule (1-NBDF), in which NBD is linked to the 1-position of D-fructose, to breast cancer (non-patent document 8).

As such, glucose derivatives and fructose derivatives bearing NBD in the molecule are known as fluorescently labeled sugar derivatives capable of imaging living cells at the cellular level individually.

In addition, a fluorescent glucose derivative obtained by linking a blue fluorescence emitting coumarin derivative molecule to D-glucose is known as well (Esculin, Fraxin, patent document 2). However, since there is no report of using a sugar derivative bearing a blue fluorescent molecule for imaging living cells at the cellular level individually, a blue fluorescence-labeled sugar derivative which can be used for imaging at the cellular level has been long-awaited.

It is known that tumor cells showing active proliferation potential require glucose as their energy source and material source for their synthesis of amino acids, nucleic acids, lipids and the like more than usual cells. Utilizing this property, a technique to diagnose cancer non-invasively from the outside of the body has already been put to practical use in the clinical medicine field, wherein $^{18}$F-radiolabeled D-glucose derivative $^{18}$F-fluoro-2-deoxy-D-glucose (FDG) is administered to a patient, and gamma ray radiated by $^{18}$F decay in FDG, taken up into tumor tissue and accumulated in the cell, is detected by a PET (positron emission tomography) apparatus. The PET examination using this radiolabeled D-glucose derivative has a issue of inability to detect micro cancer having a potential of rapid growth due to lack in spatial resolution capable of discriminating individual cells (the lower limit of spatial resolution is practically about 5 mm in PET examination). FDG faces the challenges of its short half-life (110 minutes) and the need for large-scale facilities, in addition. Further, the radiolabeled FDG which is a D-glucose derivative has a big challenge of how to avoid the fundamental problem of uptake thereof not only into tumor cells but also into normal tissue and normal cells. Particularly since adipose tissue and muscle distributing throughout the whole body, small intestinal epithelium, liver and the like take up D-glucose so strongly, discriminating them from tumor is problematic.

Other hexoses have also been tried to be applied to detect and image cancer by using their radio-labeled compounds as described above. Like D-glucose, however, its use is limited due to D-configuration thereof, and additionally, there is a problem of inability to detect a difference in individual single cells in real time with accuracy.

Application of a fluorescently labeled D-glucose derivative to tumor imaging is now underway actively in various countries intending to improve spatial resolution which is a weak point of a radiolabeling method, simultaneously avoiding the complication and danger of radiolabeling, and enabling instantaneous detection with a simple apparatus. 2-NBDG as a fluorescently labeled D-glucose derivative is one of typical molecules thereof, and it has been reported that 2-NBDG is well taken up into a tumor cell as FDG is (non-patent document 9, patent document 3, and the like), and there are trials of applying 2-NBDG to cancer diagnostic imaging (non-patent document 10, non-patent document 11).

There are active trials linking to D-glucose a fluorescent molecule emitting fluorescence of which wavelength longer than 2-NBDG such as red or near-infrared region showing higher tissue-penetrability and brighter fluorescence than 2-NBDG, for enabling fluorescence detection even from deeper tissue as compared with the case when 2-NBDG is used (non-patent document 12, non-patent document 13, non-patent document 14, and the like). However, since all of these novel fluorescent molecules have molecular weights and sizes much larger than NBD, any of fluorescent glucose derivatives to which these have been linked cannot pass through a glucose transporter (GLUT).

All fluorescent glucose derivatives so far reported including 2-NBDG are fluorescent derivatives containing D-(+)-glucose as a scaffold, and have the fundamental problem of being taken up into normal cells as well like radiolabeled FDG.

On the other hand, an idea of discriminating cancer by an approach utilizing the result of metabolic activity of cancer cells is proposed and attracting notice (non-patent document 15). A cancer cell showing brisk metabolic activity generates a large amount of acids in the form of $CO_2$ and proton ($H^+$) in the cell due to metabolism. Such acids corresponding to wastes, so to speak, are eliminated or neutralized in normal cells' case with the aid of the circulation system such as blood flow and the like, to prevent acidification in the cell. However, tissue, which is constructed to match the metabolic activity of normal cells, cannot cope with cancer cells continuing unexpected growing activity. Especially within cancer tissue remote from blood vessels, elimination and neutralization of acids tend to be insufficient, and cancer cells try to prevent intracellular acidification by developing various molecular mechanisms. A strategy targeting such a molecule particularly advanced in cancer cells might be useful for developing, for example, diagnostic pharmaceuticals which selectively discriminate cancer cells in hypoxic condition (these are known as cancer cells resistant to radiation and drugs) and a drug delivery system for carrying anti-cancer agents. As one of such target molecules, the carbonic anhydrase group expressing excessively on the plasma membrane of a cancer cell has been attracting attention (non-patent document 15).

Excess $CO_2$ as an acidic waste inevitably generated in a cell in the body by the cellular metabolic activity is eliminated by various in vivo mechanisms, to prevent acidification in the cell. A key supporting these processes is elimination of an acid by blood flow. However, in the case of cancer cells located in solid cancer dozens of microns or more away from blood vessels or abnormally growing cells in the position facing the inner cavity of a digestive tract and far from blood vessels, oxygen and glucose supply is lacking and elimination of acids as metabolites tends to be insufficient. It has recently been reported that some of such cancer cells carrying out metabolism in hypoxic and low-nutrition environment support elimination of $CO_2$ from the inside of a cell and neutralization of acids generated in a cell, by excessively expressing membrane-spanning carbonic anhydrases (CA 9 and CA 12) in the plasma membrane (non-patent document 15). Supuran and colleagues have found that a derivative of fluorescent low molecular weight compound coumarin binds to carbonic anhydrases (for example, CA 9 is supposed) expressing strongly on the plasma membrane of some cancer cells under hypoxic condition, to inhibit decarboxylating action of these enzymes (non-patent document 16, patent document 2). These coumarin derivatives are expected as one of candidates of the next generation anti-cancer agents for the reason that the derivatives attack cancer cells by destructing the pH balance of the cancer cells under the hypoxic condition (non-patent document 21).

However, carbonic anhydrases are enzymes essential for the life of all cells, and in mammals, 16 kinds of isozymes are present not only on the surface of plasma membrane but also in cytoplasm and mitochondria. Therefore, it is required that the above-described fluorescent low molecular weight compound does not cause side effect by inhibiting other types of carbonic anhydrases present in normal cells. One effective strategy is that fluorescent low molecular weight compounds such as coumarin derivatives and the like act selectively on CA9 or the like having the reaction site on the outside of the plasma membrane of a cancer cell, to prevent invasion into the cell. For this purpose, an idea is suggested in which a charge is introduced into a compound or a glycoside is prepared to give hydrophilicity to the molecule, thereby preventing penetration through plasma membrane constituted of lipid bilayer membranes (non-patent document 17). For example, Supuran and colleagues suggest that various coumarins or derivatives thereof are linked to the 1-position of a natural sugar such as D-glucose, D-mannose, D-galactose, L-rhamnose and the like, to give water solubility to the molecule, thereby providing plasma membrane impermeability (patent document 2). However, the 1-position is easily subjected to hydrolysis, and when a natural sugar is used, an influence on normal cells cannot be avoided.

In recent years, as a method for utilizing molecules showing increased expression in tumor cells, fluorescent molecular markers obtained by linking a fluorescent molecule to a molecule other than glucose are under active development. Examples thereof include those utilizing the RGD sequence and those utilizing EGF, and the like (non-patent document 18). However, such methods have a problem analogous to the method of using a derivative of a natural sugar (for example, D-glucose) as well, since even in such methods fluorescent molecules are basically taken up into normal cells though there is a difference of the degree of uptake. In contrast, a molecular marker targeting a specific tumor cell using a specific antibody or the like cannot determine other types of tumors, thus, versatility thereof is problematic.

PRIOR ART DOCUMENT

Patent Document 1: WO2010/16587
Patent Document 2: WO2012/070024
Patent Document 3: U.S. Pat. No. 6,989,140

NON-PATENT DOCUMENTS

Non-Patent Document 1: Fukuda, H. et al., Eur. J. Nucl. Med. 11: 444-448, 1986
Non-Patent Document 2: Iwashita, K., et al., Int. J. Rad. Appl. Instrum. B., 16: 247-254, 1989
Non-Patent Document 3: Wuest, M., et al., Nuc. Med. Biol. 38: 461-475, 2011
Non-Patent Document 4: Ido, T. et al., J. Labelled Compounds and Radiopharmaceuticals 14: 175-183, 1978
Non-Patent Document 5: Fukuda, H. et al., Eur. J. Nucl. Med. 7: 294-297, 1982
Non-Patent Document 6: Yamada K. et al., J. Biol. Chem. 275:22278-22283, 2000
Non-Patent Document 7: Yamada K. et al., Nat. Protoc. 2:753-762, 2007
Non-Patent Document 8: Levi, J. et al., Bioconjug. Chem. 18: 628-634 (2007)
Non-Patent Document 9: O'Neil et al, Mol. Imaging Biol. 7:388-392, 2005
Non-Patent Document 10: Sheth et al, J. Biomed. Opt. 14:064014-1-8, 2009
Non-Patent Document 11: Nitin et al, Int. J. Cancer 124; 2634-2642 (2009)
Non-Patent Document 12: Cheng Z. et al. Bioconjugate Chem. 17: 662-669, 2006
Non-Patent Document 13: Tian Y. S. et al, Angew Chem Int Ed. 48: 802-8031, 2009
Non-Patent Document 14: Kovar J L, et al, Anal. Biochem. 384:254-262, 2009
Non-Patent Document 15: Supuran, C. T., Nat. Rev. Drug Discov. 7: 168-181 (2008)
Non-Patent Document 16: Maresca, A. and Supuran, C. T., Bioorg. Med. Chem. Lett. 20: 4511-4514 (2010)
Non-Patent Document 17: Supuran, C. T., World J. Clin. Oncol. 3: 98-103 (2012)
Non-Patent Document 18: Kovar J L et al, Anal. Biochem. 367; 1-12, 2007
Non-Patent Document 19: Bristow, R. G., and Hill, R. P. Nat. Rev. Cancer 8: 180-192, 2008
Non-Patent Document 20: Denko N. C. Nat. Rev. Cancer 8: 705-713, 2008
Non-Patent Document 21: Supuran, C. T., Nat. Rev. Drug Discov. 10: 767-777 (2011)

SUMMARY OF THE INVENTION

Problem to be Solved by the Invention

The present invention has an object of providing a sugar derivative emitting blue fluorescence color which can be used for imaging of cells or intracellular molecules, and a method for imaging cells using the sugar derivative. Further, the present invention has an object of providing a method for detecting cancer cells with high accuracy by imaging, and an imaging agent used in the method.

Means for Solving the Problem

The present inventors have intensively studied in view of the above-described facts and resultantly found that living cells can be imaged using a sugar derivative having in its molecule a fluorescent molecular group composed of a specific coumarin skeleton, leading to completion of the present invention. Further, the present inventors have found that an L-glucose derivative to which a specific coumarin derivative has been linked is capable of imaging cancer cells, leading to completion of the present invention.

The present invention is as described below.

1. A composition for imaging target cells or target intracellular molecules (target intracellular molecules include molecules present in a target cell, namely present in cytoplasm or nucleus, molecules present in the plasma membrane of a target cell and molecules present on the plasma membrane of a target cell), comprising a fluorescently labeled sugar derivative having in its molecule 3-carboxy-6,8-difluoro-7-hydroxycoumarin or 3-carboxymethyl-6,8-difluoro-7-hydroxy-4-methylcoumarin as a fluorescent molecular group.

2. The composition according to the above-described 1, wherein the fluorescently labeled sugar derivative is a glucose derivative, a fructose derivative, a galactose derivative or a mannose derivative.

3. The composition according to the above-described 2, wherein the above-described fluorescent molecular group is linked to glucose, fructose, galactose or mannose via a —NH— bond.

4. The composition according to the above-described 1, wherein the fluorescently labeled sugar derivative is a molecule in which 3-carboxy-6,8-difluoro-7-hydroxycoumarin or 3-carboxymethyl-6,8-difluoro-7-hydroxy-4-methylcoumarin as a fluorescent molecular group to the 1-position, 2-position, 3-position, 4-position or 6-position of glucose (preferably, 2-position, 3-position, 4-position or 6-position, more preferably 2-position, 4-position or 6-position) is linked via a —NH— bond.

5. The composition according to the above-described 4, wherein the fluorescently labeled sugar derivative is a molecule selected from the group consisting of 2-deoxy-2-((6,8-difluoro-7-hydroxycoumarin-3-yl)carboxamido)-D-glucose, 2-deoxy-2-(2-(6,8-difluoro-7-hydroxy-4-methylcoumarin-3-yl)acetamido)-D-glucose, 2-deoxy-2-((6,8-difluoro-7-hydroxycoumarin-3-yl)carboxamido)-L-glucose and 2-deoxy-2-(2-(6,8-difluoro-7-hydroxy-4-methylcoumarin-3-yl)acetamido)-L-glucose.

6. The composition according to the above-described 1, wherein the fluorescently labeled sugar derivative is a molecule in which 3-carboxy-6,8-difluoro-7-hydroxycoumarin or 3-carboxymethyl-6,8-difluoro-7-hydroxy-4-methylcoumarin as a fluorescent molecular group is linked to the 1-position, 2-position, 3-position, 4-position or 6-position of mannose (preferably 2-position, 3-position, 4-position or 6-position, more preferably 2-position, 4-position or 6-position of mannose) via a —NH— bond.

7. The composition according to the above-described 6, wherein the fluorescently labeled sugar derivative is a molecule selected from the group consisting of 2-deoxy-2-((6,8-difluoro-7-hydroxycoumarin-3-yl)carboxamido)-D-mannose, 2-deoxy-2-((6,8-difluoro-7-hydroxycoumarin-3-yl)carboxamido)-L-mannose, 2-deoxy-2-(2-(6,8-difluoro-7-hydroxy-4-methylcoumarin-3-yl)acetamido)-D-mannose and 2-deoxy-2-(2-(6,8-difluoro-7-hydroxy-4-methylcoumarin-3-yl)acetamido)-L-mannose.

8. A method for imaging target cells or target intracellular molecules (target intracellular molecules include molecules present in a target cell, namely present in cytoplasm or nucleus, molecules present in the plasma membrane of a target cell and molecules present on the plasma membrane of a target cell), comprising the following steps:
(a) a step of contacting the composition according to any one of the above-described 1 to 7 with target cells (target cells include also cells present in tissue, in addition to cells themselves), and
(b) a step of detecting the above-described sugar derivative present in the above-described target cell (including inside of a target cell, namely in cytoplasm or nucleus, in the plasma membrane of a target cell and on the plasma membrane of a target cell).

9. A fluorescently labeled sugar derivative in which 3-carboxy-6,8-difluoro-7-hydroxycoumarin or 3-carboxymethyl-6,8-difluoro-7-hydroxy-4-methylcoumarin as a fluorescent molecular group is linked to a sugar selected from the group consisting of glucose, fructose, galactose and mannose via a —NH— bond.

10. A fluorescently labeled sugar derivative selected from the group consisting of 2-deoxy-2-((6,8-difluoro-7-hydroxycoumarin-3-yl)carboxamido)-D-glucose, 2-deoxy-2-(2-(6,8-difluoro-7-hydroxy-4-methylcoumarin-3-yl)acetamido)-D-glucose, 2-deoxy-2-((6,8-difluoro-7-hydroxycoumarin-3-yl)carboxamido)-L-glucose, 2-deoxy-2-(2-(6,8-difluoro-7-hydroxy-4-methylcoumarin-3-yl)acetamido)-L-glucose, 2-deoxy-2-((6,8-difluoro-7-hydroxycoumarin-3-yl)carboxamido)-D-mannose, 2-deoxy-2-(2-(6,8-difluoro-7-hydroxy-4-methylcoumarin-3-yl)acetamido)-D-mannose, 2-deoxy-2-((6,8-difluoro-7-hydroxycoumarin-3-yl)carboxamido)-L-mannose and 2-deoxy-2-(2-(6,8-difluoro-7-hydroxy-4-methylcoumarin-3-yl)acetamido)-L-mannose.

11. A fluorescently labeled sugar derivative which is 2-deoxy-2-((6,8-difluoro-7-hydroxycoumarin-3-yl)carboxamido)-D-glucose or 2-deoxy-2-((6,8-difluoro-7-hydroxycoumarin-3-yl)carboxamido)-D-mannose.

12. A method for detecting cancer or cancer cells, comprising the following steps:
(a) a step of contacting a composition containing a fluorescently labeled L-glucose derivative in which 3-carboxy-6,8-difluoro-7-hydroxycoumarin or 3-carboxymethyl-6,8-difluoro-7-hydroxy-4-methylcoumarin is linked as a fluorescent molecular group with target cells (target cells include also cells present in tissue, in addition to cells themselves), and
(b) a step of detecting the above-described L-glucose derivative present in the above-described target cell (including inside of a target cell, namely in cytoplasm or nucleus, in the plasma membrane of a target cell and on the plasma membrane of a target cell).

13. The detection method according to the above-described 12, wherein the above-described fluorescently labeled L-glucose derivative is a molecule in which 3-carboxy-6,8-difluoro-7-hydroxycoumarin or 3-carboxymethyl-6,8-difluoro-7-hydroxy-4-methylcoumarin as a fluorescent molecular group is linked to the 1-position, 2-position, 3-position, 4-position or 6-position of L-glucose (preferably 2-position, 3-position, 4-position or 6-position, more preferably 2-position, 4-position or 6-position of L-glucose) via a —NH— bond.

14. The detection method according to the above-described 12, wherein the above-described fluorescently labeled L-glucose derivative is 2-deoxy-2-((6,8-difluoro-7-hydroxycoumarin-3-yl)carboxamido)-L-glucose or 2-deoxy-2-(2-(6,8-difluoro-7-hydroxy-4-methylcoumarin-3-yl) acetamido)-L-glucose.

15. The detection method according to any one of the above-described 12 to 14, wherein detection in the above-described step (a) is conducted by imaging a target cell.

16. The detection method according to any one of the above-described 12 to 15, wherein the composition in the above-described step (a) further contains one in which sulforhodamine (preferably sulforhodamine 101, sulforhodamine B) is linked to the 2-position of 2-amino-2-deoxy-L-glucose via sulfonamide linkage and the above-described step (b) is a step for detecting (one or both) fluorescently labeled L-glucose derivatives present in a target cell.

17. The detection method according to any one of the above-described 12 to 16, wherein the target cell is a cell in a tumor cell cluster.

18. An agent for imaging target cancer cells (target cells include also cancer cells present in tissue, in addition to cells themselves) (for example, imaging cancer cells by uptake of a fluorescently labeled L-glucose derivative into target cancer cells (including inside of a target cell, namely in cytoplasm or nucleus, in the plasma membrane of a target cell and on the plasma membrane of a target cell)), comprising a fluorescently labeled L-glucose derivative in which 3-carboxy-6,8-difluoro-7-hydroxycoumarin or 3-carboxymethyl-6,8-difluoro-7-hydroxy-4-methylcoumarin as a fluorescent molecular group is linked.

19. The imaging agent according to the above-described 18, wherein the above-described fluorescently labeled L-glucose derivative is a fluorescently labeled L-glucose derivative in which 3-carboxy-6,8-difluoro-7-hydroxycoumarin or 3-carboxymethyl-6,8-difluoro-7-hydroxy-4-methylcoumarin as a fluorescent molecular group is linked to the 1-position, 2-position, 3-position, 4-position or 6-position of L-glucose (preferably 2-position, 3-position, 4-position or 6-position, more preferably 2-position, 4-position or 6-position of L-glucose) via a —NH— bond.

20. The imaging agent according to the above-described 18, wherein the above-described fluorescently labeled L-glucose derivative is 2-deoxy-2-((6,8-difluoro-7-hydroxycoumarin-3-yl)carboxamido)-L-glucose or 2-deoxy-2-(2-(6,8-difluoro-7-hydroxy-4-methylcoumarin-3-yl)acetamido)-L-glucose.

21. The imaging agent according to any one of the above-described 18 to 20, wherein the above-described imaging agent further contains one in which sulforhodamine (preferably sulforhodamine 101 or sulforhodamine B) is linked to the 2-position of 2-amino-2-deoxy-L-glucose via sulfonamide linkage of.

22. A fluorescently labeled L-glucose derivative which is 2-deoxy-2-((6,8-difluoro-7-hydroxycoumarin-3-yl)carboxamido)-L-glucose or 2-deoxy-2-(2-(6,8-difluoro-7-hydroxy-4-methylcoumarin-3-yl)acetamido)-L-glucose.

23. A kit for detecting cancer cells, comprising the imaging agent according to any one of the above-described 18 to 21.

24. A method of diagnosing a target cell as cancer, by detecting cancer cells using the detection method according to any one of the above-described 12 to 17.

Effect of the Invention

The present invention can provide a blue imaging agent capable of discriminating cells or intracellular molecules at a high contrast. The present invention can further provide a method capable of discriminating cancer cells at a high contrast and an imaging agent for the method.

DESCRIPTION OF EMBODIMENTS

Figure 1:
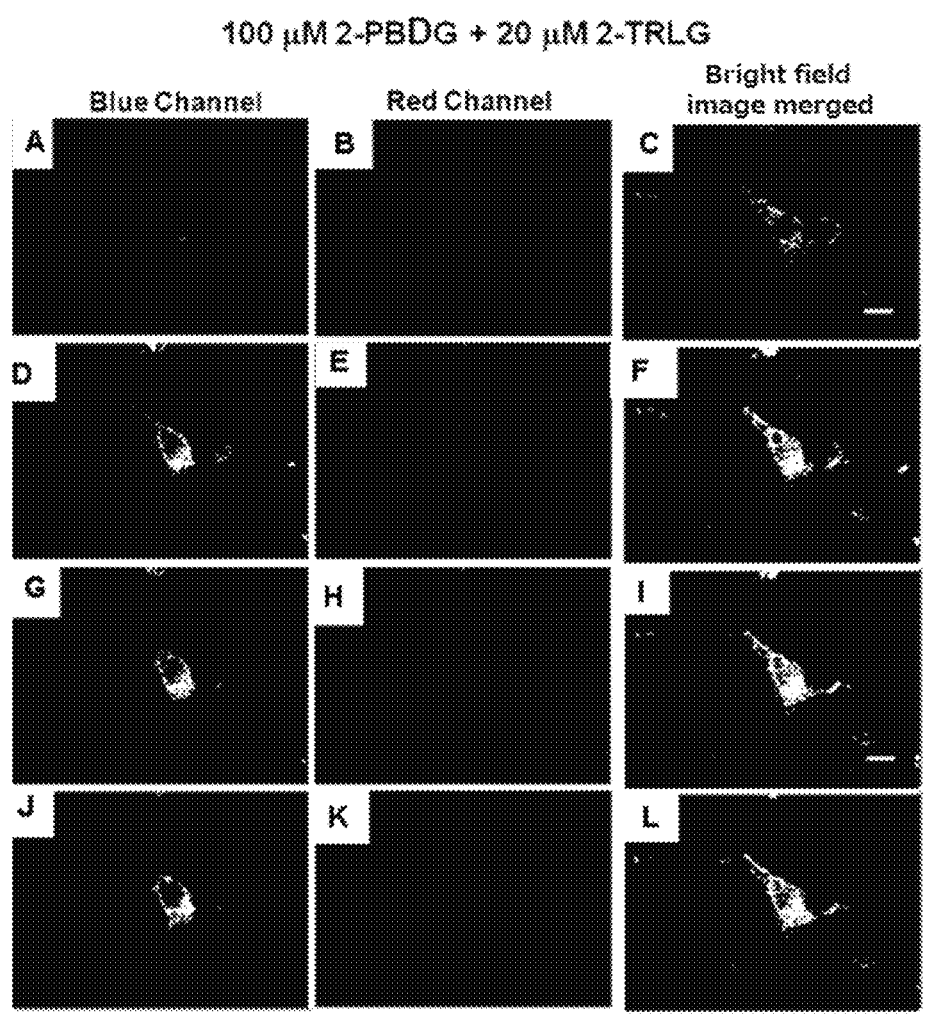
FIGS. 1A-1L show the results of administration of a mixed solution of a D-glucose derivative (2-PBDG: 100 µM) emitting blue fluorescence and an L-glucose derivative (2-TRLG: 20 µM) emitting red fluorescence to normal neurons.

In one embodiment, the present invention provides an imaging agent for imaging cells or intracellular molecules using a sugar derivative to which a specific coumarin derivative (Pacific Blue or Marina Blue) has been linked, and a method for imaging cells or intracellular molecules using the imaging agent.

In one embodiment, the present invention provides a fluorescently labeled sugar derivative to which a specific coumarin derivative (Pacific Blue or Marina Blue) has been linked, which can be used in the above-described imaging agent.

In another embodiment, the present invention provides an imaging agent for detecting cancer cells using a fluorescently labeled L-glucose derivative obtained by linking a specific coumarin derivative (Pacific Blue or Marina Blue) to L-glucose, and a method for detecting cancer cells using the imaging agent.

In another embodiment, the present invention provides a fluorescently labeled L-glucose derivative obtained by linking a coumarin derivative (Pacific Blue or Marina Blue), which can be used in the above-described imaging agent.

According to the present invention, by bringing a composition containing a fluorescently labeled sugar derivative having in its molecule 3-carboxy-6,8-difluoro-7-hydroxycoumarin (Pacific Blue) or 3-carboxymethyl-6,8-difluoro-7-hydroxy-4-methylcoumarin (Marina Blue) as a fluorescent molecular group (hereinafter, referred to as "composition of the present invention" or "imaging agent of the present invention"), as a reagent, into contact with target cells, target cells or target intracellular molecules (target intracellular molecules include molecules present in a target cell, namely in cytoplasm or nucleus, molecules present in the plasma membrane of a target cell and molecules present on the plasma membrane of a target cell) can be imaged at individual cell level. Further, according to the present invention, by bringing the composition of the present invention into contact with tissue containing target cells and performing imaging, cells or intracellular molecules in the tissue can be imaged at individual cell level.

The sugar in the fluorescently labeled sugar derivative of the present invention may be any sugar providing it is taken up into living cells (normal cells or abnormal cells), and glucose, fructose, galactose or mannose is preferable. The sugar includes a D-isomer and an L-isomer, and in the present invention, any of them can be used. By use of a D-isomer and an L-isomer, the target can be imaged at cell level based on the DL steric configurations of these various sugars to elucidate its function, and further, discrimination of normal cells and abnormal cells is made possible.

Further, also microorganisms having natures different from mammalian cells in recognition, transport and metabolism of the sugar relating to the D and L steric configurations can be analyzed for its function, by performing imaging at the cellular level using a D- or L-configured fluorescently labeled sugar derivative.

Moreover, according to the present invention, by bringing a composition containing a fluorescently labeled L-glucose derivative having in its molecule 3-carboxy-6,8-difluoro-7-hydroxycoumarin (Pacific Blue) or 3-carboxymethyl-6,8-difluoro-7-hydroxy-4-methylcoumarin (Marina Blue) as a fluorescent molecular group (hereinafter, referred to as "composition of the present invention" or "imaging agent of the present invention"), as a reagent, into contact with target cells, whether the target cell is a cancer cell or not can be determined. Also, according to the present invention, by bringing the composition of the present invention into contact with tissue containing target cells and performing imaging, cancer cells in the tissue can be detected. Still more, according to the present invention, by administering the composition of the present invention to a living body and performing imaging, cancer cells or tissue containing these cells can be detected, and this method is useful as a method for detecting cancer.

The composition of the present invention includes any forms of compositions which can be applied to cells containing the fluorescently labeled sugar derivative of the present invention, and the form includes a solution, a gel and the like and is not particularly restricted providing application to cells is possible. Components in the composition can be contained without specific restriction providing they are suitable for application to cells. For example, the fluorescently labeled sugar derivative of the present invention can be dissolved in a buffer solution or a medium for cell cultivation and applied to cells.

I. Imaging of Cell or Intracellular Molecule Using Fluorescently Labeled Sugar Derivative (I-1) Fluorescently Labeled Sugar Derivative The fluorescently labeled sugar derivative of the present invention emitting blue fluorescence, which can be used for imaging cells or intracellular molecules, is a fluorescently labeled sugar derivative obtained by linking 3-carboxy-6,8-difluoro-7-hydroxycoumarin (Pacific Blue) or 3-carboxymethyl-6,8-difluoro-7-hydroxy-4-methylcoumarin (Marina Blue) as a fluorescent molecular group to a sugar, preferably, glucose, fructose, galactose or mannose.

The linking site of a fluorescent molecular group in the sugar derivative is not particularly restricted providing it can be synthesized by the method described in the present specification or by an ordinary method, and in the case of glucose, the site includes the 1-position, 2-position, 3-position, 4-position or 6-position (preferably 2-position, 3-position, 4-position or 6-position, more preferably 2-position, 4-position or 6-position), in the case of fructose, the site includes the 1-position, 3-position, 4-position, 5-position or 6-position (preferably 1-position, 5-position or 6-position, more preferably 1-position), in the case of galactose, the site includes the 1-position, 2-position, 3-position, 4-position or 6-position (preferably 2-position, 3-position, 4-position or 6-position, more preferably 2-position, 3-position or 6-position), and in the case of mannose, the site includes the 1-position, 2-position, 3-position, 4-position or 6-position (preferably 2-position, 3-position, 4-position or 6-position, more preferably 2-position, 4-position or 6-position).

The linkage of the above-described fluorescent molecular group to a sugar will be illustrated below referring to glucose, and the same shall apply also to other sugars.

The linking position of the above-described fluorescent molecular group to a sugar is not particularly restricted, and the group can be linked to any position according to an ordinary method. For example, in the case of linkage to glucose, the above-described fluorescent molecular group can be linked to any of the 1-position, 2-position, 3-position, 4-position or 6-position of glucose, preferably, to the 2-position, 3-position, 4-position or 6-position. Linking can be conducted, for example, by using glucosamine via —NH— at the 2-position.

As the glucosamine, D-glucosamine or L-glucosamine can be used. As the D-glucosamine, D-glucosamine synthesized or commercially available D-glucosamine can be used. L-glucosamine can be synthesized by a method described in WO 2010/16587 or a method described in the specification as filed of PCT/JP2012/58439 (Descriptions in the publication and the specification as filed are incorporated herein as a part of the present specification). The method described in the specification as filed of PCT/JP2012/58439 is as described below.

[Chemical formula 1]

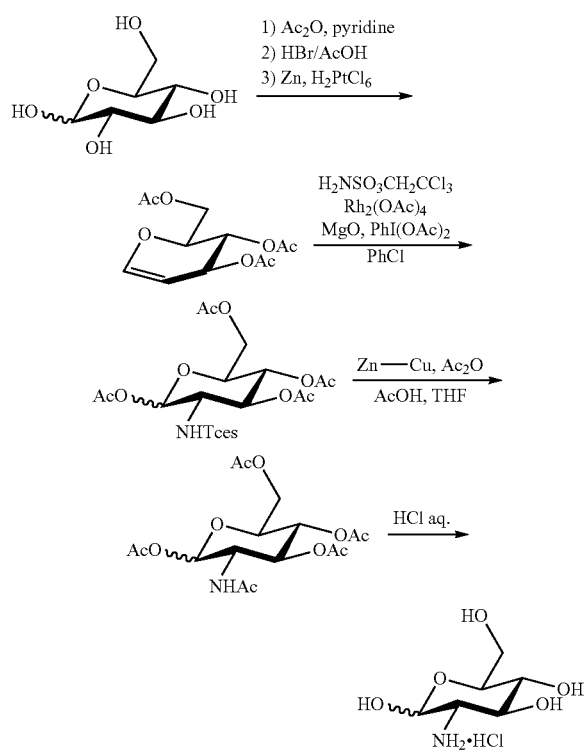

The fluorescently labeled glucose derivative of the present invention obtained by linking Pacific Blue (PB) to glucose is preferably represented by the following formula (1) or (2).

[Chemical formula 2]

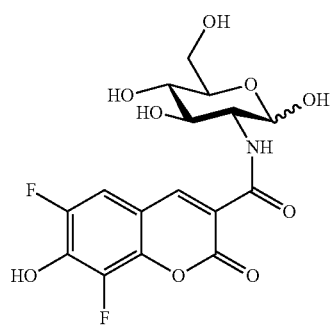

(1)

-continued

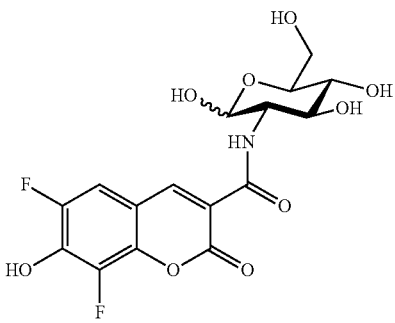

(2)

The formula (1) (obtained by linking Pacific Blue (PB) to D-glucosamine: referred to as 2-PBDG) and the formula (2) (obtained by linking Pacific Blue (PB) to L-glucosamine: referred to as 2-PBLG) are in enantiomeric correlation, and the maximum excitation wavelength (Ex max) and the maximum emission wavelength (Em max) are 403 nm (Ex max) and 453 nm (Em max) for both the compounds.

The glucose derivative emitting blue fluorescence of the present invention can be dissolved in any solutions, for example, solvents such as DMSO and the like and used, and is stable also in solvents and solutions used for imaging cells or intracellular molecules, thus, the glucose derivative is suitable as an imaging agent.

(I-2) Imaging of Cell or Intracellular Molecule

The target cell as the subject of imaging using the sugar derivative emitting blue fluorescence of the present invention is not particularly restricted, and cells derived from mammals, cells of microorganisms such as *E. coli*, yeast and the like, cells of plants, fertilized ovum and the like can be used as the subject, and the target cell may be any form of cell such as cells isolated from living bodies, cells present in tissue isolated from a living body, cells present in tissue of a living body, primary cultured cells after isolating from a living body, established cells and the like. Further, the cell as the subject may be a normal cell or an abnormal cell (for example, cancer cell).

In the method of imaging cells or intracellular molecules of the present invention, detection of the fluorescently labeled sugar derivative of the present invention taken up into a cell can be conducted by a method usually used for detecting fluorescence. For example, this can be carried out as described below. Regarding detection of the fluorescently labeled sugar derivative present in a cell in the method of the present invention, the fluorescence of the target cell is measured previously, then, a fluorescently labeled sugar derivative is brought into contact with the target cell for a certain time, then, this is washed away, the fluorescence of the target cell is measured again, and an increase in fluorescence intensity with respect to the fluorescence intensity of the target cell before contact can be used for evaluation. During contact of the fluorescently labeled sugar derivative, cells may be imaged using a suitable apparatus capable of discriminating the inside of a cell, the plasma membrane and the outside of a cell such as a confocal microscope and the like. By recognizing fluorescence intensity as an image, cells containing the fluorescently labeled sugar derivative of the present invention in its cell can be imaged and detection of cells or intracellular molecules can be conducted. Further, evaluation may be performed based on the sum of fluorescence intensities manifested by a lot of cells or distribution of the fluorescence intensities, using a fluorescence plate reader, flow cytometry and the like.

By use of the fluorescently labeled sugar derivative of the present invention, detection and/or imaging of cells and/or intracellular molecules with blue color is made possible. The fluorescently labeled sugar derivative of the present invention can be used simultaneously with sugar derivatives having other fluorescent chromophore groups, for example, 2-NBDG and 2-NBDLG emitting green fluorescence and/or 2-TRLG emitting red fluorescence. 2-NBDG, 2-NBDLG and 2-TRLG are described in WO 2010/16587 (these are incorporated herein as a part of the present specification). By this, evaluation with two colors or three colors is made possible.

II. Detection or Imaging of Cancer Cell Using L-Glucose Derivative (II-1)

The L-glucose derivative emitting blue fluorescence of the present invention which can be used for detection or imaging of cancer cells is a molecule obtained by linking 3-carboxy-6,8-difluoro-7-hydroxycoumarin (Pacific Blue) or 3-carboxymethyl-6,8-difluoro-7-hydroxy-4-methylcoumarin (Marina Blue) as a fluorescent molecular group to L-glucose. For linkage to L-glucose, the above-described fluorescent molecular group can be linked to any of the 1-position, 2-position, 3-position, 4-position or 6-position of glucose, preferably to the 2-position, 3-position, 4-position or 6-position, more preferably to the 2-position, 4-position or 6-position. Linking can be conducted, for example, by using glucosamine via —NH— at the 2-position.

The fluorescently labeled L-glucose derivative of the present invention is preferably represented by the following formula (2).

[Chemical formula 3]

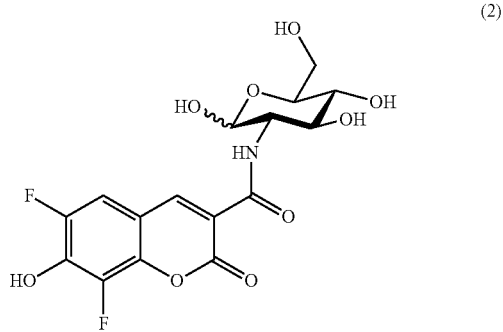

(2)

(II-2) Detection or Imaging of Cancer Cell

Cancer continues to proliferate endlessly to impart various disadvantages to a living body, and particularly, the presence of cancer cells showing resistance to anti-cancer agents and radiation therapy in cancer has been indicated recently, and such special cancer cells have a molecular mechanism coping with hypoxic and low-nutrition environment wherein normal cells cannot survive (see, non-patent document 19).

The fluorescently labeled L-glucose derivative of the present invention is a compound obtained by linking L-glucose having a nature of no uptake into normal cells to a specific coumarin derivative (Pacific Blue or Marina Blue) acting as a key molecule. Since coumarin and derivatives thereof bind to a carbonic anhydrase expressed excessively in a cancer cell under hypoxic and low-nutrition environment and disturb its function, it is possible to selectively visualize and at the same time interfere with function of above-described specific cancer cells by administering the fluorescently labeled L-glucose derivative of the present invention to a cell group including cancer cells, while minimizing the influence on normal cells.

The cell targeted by the method of the present invention includes, for example, cancer cells under energy deficient condition such as low-oxygen and low-nutrition within solid cancer or a cancer cell mass showing two-dimensional or three-dimensional remarkable proliferation in an inner cavity of a digestive tract and the like (non-patent document 20). The form of the target cell is not particularly restricted and may be any cellular form such as cells isolated from a living body, cells present in tissue isolated from a living body, cells present in tissue of a living body, primary cultured cells after isolation from a living body, established cells and the like.

The cell strongly-positive to the fluorescently labeled L-glucose derivative of the present invention (for example, 2-PBLG) is believed to be a cancer cell which has acquired an outstanding nature of response capability to the hypoxic environment, and such cancer cell is possibly a cell which has acquired one ability of surviving even under different environment at metastasized area different from the environment where the cancer cell is originally present, thus, such a cell can be selectively discriminated and visualized using the fluorescently labeled L-glucose derivative of the present invention.

In the method for detecting cancer of the present invention, the fluorescently labeled L-glucose derivative of the present invention (L-glucose derivative having Pacific Blue or Marina Blue in the molecule) can be used simultaneously with other fluorescently labeled L-glucose derivatives, for example, 2-[N-(7-nitrobenz-2-oxa-1,3-diazol-4-yl)amino]-2-deoxy-L-glucose (2-NBDLG) and 2-TexasRed-2-amino-2-deoxy-L-glucose (2-TRLG), and by this, the condition of cancer cells and the whole tumor cell cluster containing cancer cells can be evaluated together.

The method for detecting cancer of the present invention and the imaging agent for the method can be used for recognition of the presence of hypoxia-resistant tumor cells, evaluation of the condition thereof and discrimination from normal cells, targeting tissue excised in operation, intraoral tumors, digestive system tumors obtained by using an endoscope, gynecologic tumors such as uterocervical cancer and the like, biopsy specimen obtained at biopsy and other diagnosis of lung and various organs. By this, detailed cell evaluation at the cellular level can be attained quickly with a simple fluorescence apparatus, and this is effective as the guideline for selecting the therapeutic method, for the judgment of the therapeutic efficiency of a drug and the like, and for determination of suitable extent of operation after exposure of the affected area, and the like.

In the detection method of the present invention, the detection of a fluorescently labeled L-glucose derivative present in a cancer cell can be evaluated, for example, as follows: the fluorescence of the target cell is measured beforehand, then a fluorescently labeled L-glucose derivative is brought into contact with the target cell for a certain time, then, this is washed away, the fluorescence of the target cell is measured again, and an increase in the fluorescence intensity in comparison with the fluorescence intensity of the target cell before contact can be used for evaluation. The detection of cancer cells or suspected cells can be made by imaging cells containing the fluorescently labeled L-glucose derivative in the cell and recognizing fluorescence intensity as an image. The evaluation may also be performed based on the sum of fluorescence intensities exhibited by a large number of cells tested or distribution of fluorescence intensities, using a fluorescence plate reader, a flow cytometry and the like. When the fluorescently labeled L-glucose derivative of the present invention is administered to blood vessels such as vein and the like, systemic imaging can be performed, and additionally, cell imaging can also be performed by locally administering the derivative to tissue to be observed.

As apparent from the above-described explanations, the fluorescently labeled L-glucose derivative of the present invention is useful for detecting cancer cells, and also useful, for example, as an active constituent of an imaging agent for visualizing cancer cells. The fluorescently labeled L-glucose derivative may be dissolved in a solvent (physiological saline for injection and the like) for dissolving this and provided in the form of a solution, or may be combined with a solvent for dissolving this and provided in the form of a kit by which the derivative is dissolved to prepare a solution in use. The concentration of the fluorescently labeled L-glucose derivative in a solution may be prepared, for example, in the range of 1 nM to 100 mM. It may also be permissible to further improve accuracy of the evaluation by combining the method of using the labeled L-glucose derivative of the present invention for detection of cancer cells with a method known in the area of fluorescence detection or cell detection.

EXAMPLES

The present invention will be illustrated in detail by examples below, but the present invention is not construed to be limited to the following descriptions.

Example 1: Synthesis of Compound (1) Synthesis of Fluorescently Labeled Sugar Derivative Synthesis of 2-PBDG (2-Deoxy-2-((6,8-difluoro-7-hydroxycoumarin-3-yl)carboxamido)-D-glucose)

2-PBDG represented by the following formula was synthesized as described below.

[Chemical formula 4]

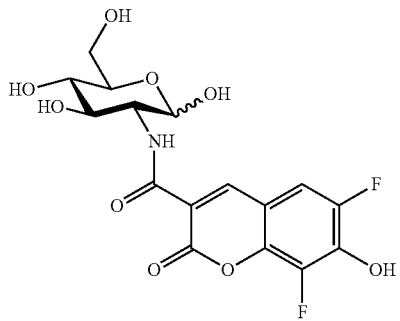

D-glucosamine hydrochloride (47.7 mg) was dissolved in dimethylformamide/water=10/3 (1.3 mL) and the solution was stirred. Pacific Blue™ Succinimidyl Ester (50 mg) was added, and further, triethylamine (40.8 μL) was added. Five hours later, acetic acid was added for neutralization, and water was added and the resultant solution was allowed to pass through a membrane filter. The filtrate and the washing solution were combined and purified by HPLC. The intended fractions were collected and freeze dried.

Yielded amount: 42.9 mg
Yielded: 72%
$^1$H-NMR (400 MHz, deuterated methanol, ppm):
δ9.11 (d, 0.8H, J=9.2 Hz, NH), δ8.98 (d, 0.2H, J=9.2 Hz, NH), δ8.77 (s, 1H, H4'), δ7.43 (dd, 1H, J=10.3 Hz and J=2.1 Hz, H5'), δ5.18 (d, 0.8H, J=3.2 Hz, H-1α), δ4.77 (d, 0.2H, J=8.7 Hz, H-1β), δ3.35-δ4.10 (m, 6H, H-2, H-3, H-4, H-5, H-6, H-6).
ESI-MS: calcd for $C_{16}H_{16}F_2NO_9$ [M+H]$^+$ 404.07. found 404.0.
Maximum excitation wavelength: 403 nm
Maximum emission wavelength: 453 nm Synthesis of 2-PBLG (2-Deoxy-2-((6,8-difluoro-7-hydroxycoumarin-3-yl)carboxamido)-L-glucose)

2-PBLG represented by the following formula was synthesized as described below.

[Chemical formula 5]

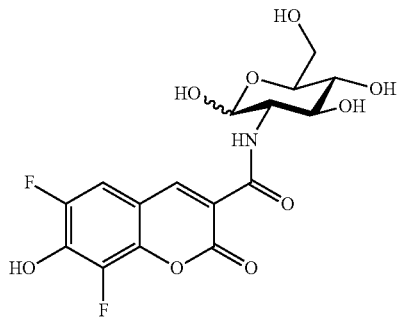

L-glucosamine hydrochloride (12.7 mg) was dissolved in dimethylformamide/water=10/1 (1.1 mL) and the solution was stirred. Pacific Blue™ Succinimidyl Ester (10 mg) was added, and further, triethylamine (12.3 μL) was added. Three hours later, acetic acid was added for neutralization, and water was added and the resultant solution was allowed to pass through a membrane filter. The filtrate and the washing solution were combined and purified by HPLC. The intended fractions were collected and freeze dried.

Yielded amount: 9.2 mg
Yielded: 77%
$^1$H-NMR (400 MHz, deuterated methanol, ppm):
δ9.11 (d, 0.8H, J=9.2 Hz, NH), δ8.98 (d, 0.2H, J=9.2 Hz, NH), δ8.77 (s, 1H, H4'), δ7.43 (dd, 1H, J=10.3 Hz and J=2.1 Hz, H5'), δ5.18 (d, 0.8H, J=3.2 Hz, H-1α), δ4.77 (d, 0.2H, J=8.7 Hz, H-1β), δ3.35-δ4.10 (m, 6H, H-2, H-3, H-4, H-5, H-6, H-6).
ESI-MS: calcd for $C_{16}H_{16}F_2NO_9$ [M+H]$^+$ 404.07. found 404.0.
Maximum excitation wavelength: 403 nm
Maximum emission wavelength: 453 nm Synthesis of Other PBDG and PBLG Pacific Blue-labeled D-glucose derivatives obtained by linking a fluorescent molecular group to the 3-position, 4-position or 6-position of D-glucose can be synthesized by using 3-amino-3-deoxy-D-glucose, 4-amino-4-deoxy-D-glucose or 6-amino-6-deoxy-D-glucose as a raw material and introducing Pacific Blue into the 3-position, 4-position or 6-position of D-glucose, respectively, according to an ordinary method. Further, introduction of a fluorescent molecular group into the 1-position is possible by synthesizing a 1-azide body as an intermediate and reducing it, then, immediately fluoresceinating this.

The Pacific Blue-labeled L-glucose derivative can be synthesized in the same manner using aminodeoxy-L-glucose as a raw material.

Synthesis of 2-PBDM (2-Deoxy-2-((6,8-difluoro-7-hydroxycoumarin-3-yl)carboxamido)-D-mannose)

2-PBDM represented by the following formula was synthesized as described below.

[Chemical formula 6]

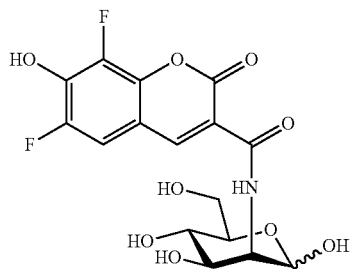

D-mannosamine hydrochloride (9.5 mg) was dissolved in water (40 μL), and dimethylformamide (100 μL) and triethylamine (10.3 μL) were added to this and the mixture was stirred at room temperature. Pacific Blue™ Succinimidyl Ester (10 mg) and dimethylformamide (800 μL) were added and the mixture was stirred at room temperature. One hour and 30 minutes after, triethylamine (5.2 μL) was added and the mixture was stirred at room temperature. One hour and 30 minutes after, acetic acid was added for neutralization, and the resultant solution was allowed to pass through a membrane filter. The filtrate and the washing solution were combined and purified by HPLC. The intended fractions were collected and freeze dried.

Yielded amount: 10.5 mg

Yielded: 88%

$^1$H-NMR (400 MHz, deuterated methanol, ppm):

δ9.14 (m, 0.5H, NH), δ8.74 (m, 1H, Ar), δ7.87 (s, 0.5H, NH), δ7.40 (m, 1H, Ar), δ5.14 (d, 0.5H, J=1.8 Hz, H-1), δ4.93 (d, 0.5H, J=1.4 Hz, H-1), δ3.43-δ4.57 (m, 6H, H-2, H-3, H-4, H-5, H-6, H-6).

ESI-MS: calcd for $C_{16}H_{16}F_2NO_9$ [M+H]$^+$ 404.07. found 404.0.

Maximum excitation wavelength: 404 nm

Maximum emission wavelength: 453 nm

Synthesis of 2-PBLM (2-Deoxy-2-((6,8-difluoro-7-hydroxycoumarin-3-yl)carboxamido)-L-mannose)

2-PBLM represented by the following formula can be synthesized by the same manner as for the above-described 2-PBDM as its enantiomer.

[Chemical formula 7]

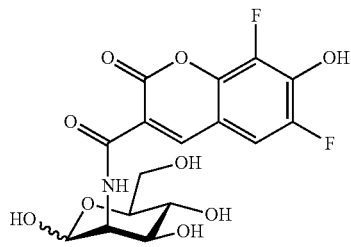

Synthesis of Other PBDM and PBLM

Pacific Blue-labeled D-mannose derivatives obtained by linking a fluorescent molecular group to the 3-position, 4-position or 6-position of D-mannose can be synthesized by using 3-amino-3-deoxy-D-mannose, 4-amino-4-deoxy-D-mannose or 6-amino-6-deoxy-D-mannose as a raw material and introducing Pacific Blue into the 3-position, 4-position or 6-position of D-mannose, respectively, according to an ordinary method. Further, introduction of a fluorescent molecular group into the 1-position is possible by synthesizing a 1-azide body as an intermediate and reducing it, then, immediately fluoresceinating this.

The Pacific Blue-labeled L-mannose derivative can be synthesized in the same manner by using aminodeoxy-L-mannose as a raw material.

Synthesis of 2-MBDG (2-Deoxy-2-(2-(6,8-difluoro-7-hydroxy-4-methylcoumarin-3-yl)acetamido)-D-glucose)

2-MBDG represented by the following formula was synthesized as described below.

[Chemical formula 8]

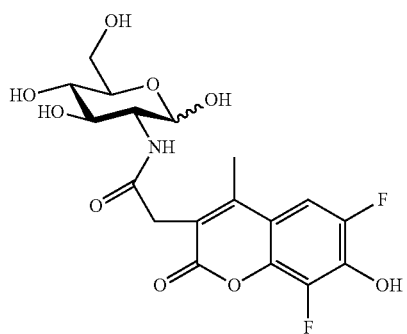

D-glucosamine hydrochloride (11.7 mg) was dissolved in water (50 μL), and dimethylformamide (50 μL) was added and the mixture was stirred. To this was added triethylamine (11.3 μL), subsequently, a dimethylformamide solution of Marina Blue™ Succinimidyl Ester (10 mg) was added, and the mixture was stirred at room temperature. Acetic acid was added for neutralization, then, the resultant solution was allowed to pass through a membrane filter, and the filtrate and the washing solution were combined and purified by HPLC. The intended fractions were collected and freeze dried.

Yielded amount: 11.4 mg

Yielded: 97%

$^1$H-NMR (400 MHz, deuterated methanol, ppm):

δ7.89 (d, 0.4H, J=10.1 Hz, NH), δ7.37 (dd, 1H, J=11.9 Hz and J=2.3 Hz, H5'), δ5.11 (d, 0.7H, J=3.2 Hz, H-1α), δ4.61

(d, 0.3H, J=7.8 Hz, H-1β), δ3.34-δ3.87 (m, 8H, H-2, H-3, H-4, H-5, H-6, H-6, C3'-CH$_2$), δ2.41 (s, 3H, C4'-CH$_3$)

ESI-MS: calcd for C$_{18}$H$_{20}$F$_2$NO$_9$ [M+H]$^+$ 432.10. found 432.1.

Maximum excitation wavelength: 364 nm

Maximum emission wavelength: 458 nm

Synthesis of 2-MBLG (2-Deoxy-2-(2-(6,8-difluoro-7-hydroxy-4-methylcoumarin-3-yl)acetamido)-L-glucose)

2-MBLG represented by the following formula was synthesized as described below.

[Chemical formula 9]

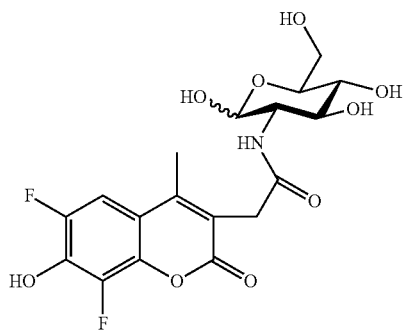

L-glucosamine hydrochloride (7.1 mg) was dissolved in water (56 μL), and dimethylformamide (400 μL) was added and the mixture was stirred. Marina Blue™ Succinimidyl Ester (10 mg) and dimethylformamide (1.2 mL) were added, subsequently, triethylamine (8.3 μL) was added and the mixture was stirred at room temperature. One hour and 30 minutes after, L-glucosamine hydrochloride (1.8 mg) and triethylamine (1.1 μL) were added additionally and the mixture was stirred at room temperature. Further one hour after, triethylamine (1.9 μL) was added additionally and the mixture was stirred at room temperature. Thirty minutes after, acetic acid was added for neutralization, then, the resultant solution was allowed to pass through a membrane filter, and the filtrate and the washing solution were combined and purified by HPLC. The intended fractions were collected and freeze dried.

Yielded amount: 10.0 mg

Yielded: 85%

$^1$H-NMR (400 MHz, deuterated methanol, ppm):

δ7.86 (d, 0.2H, J=9.2 Hz, NH), δ7.36 (dd, 1H, J=11.9 Hz and J=2.3 Hz, H5'), δ5.10 (d, 0.7H, J=3.2 Hz, H-1α), δ4.61 (d, 0.3H, J=8.2 Hz, H-1β), δ3.35-δ3.86 (m, 8H, H-2, H-3, H-4, H-5, H-6, H-6, C3'-CH$_2$), δ2.40 (s, 3H, C4'-CH$_3$)

ESI-MS: calcd for C$_{18}$H$_{20}$F$_2$NO$_9$ [M+H]$^+$ 432.10. found 432.1.

Maximum excitation wavelength: 365 nm

Maximum emission wavelength: 458 nm

Synthesis of other MBDG and MBLG

Other MBDG and MBLG having Marina Blue at the 1-position, 3-position, 4-position or 6-position can be synthesized in the same manner as for PBDG and PBLG.

Synthesis of 2-MBDM (2-Deoxy-2-(2-(6,8-difluoro-7-hydroxy-4-methylcoumarin-3-yl)acetamido)-D-mannose)

In the same manner as the synthesis method of 2-MBDG, 2-MBDM can be synthesized using D-mannosamine hydrochloride instead of D-glucosamine hydrochloride used for synthesis of 2-MBDG.

Synthesis of 2-MBLM (2-Deoxy-2-(2-(6,8-difluoro-7-hydroxy-4-methylcoumarin-3-yl)acetamido)-L-mannose)

In the same manner as the synthesis method of 2-MBLG, 2-MBLM can be synthesized using L-mannosamine hydrochloride instead of L-glucosamine hydrochloride used for synthesis of 2-MBLG.

Comparative Example 1: Synthesis of Comparative Compound

Synthesis of 2-HCDG (2-Deoxy-2-((7-hydroxycoumarin-3-yl) carboxamido)-D-glucose)

2-HCDG represented by the following formula was synthesized as described below.

[Chemical formula 10]

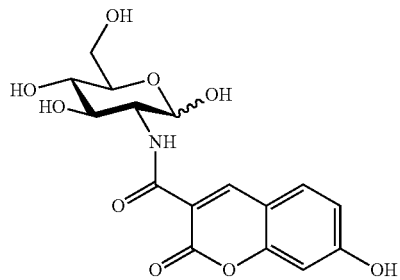

D-glucosamine hydrochloride (11.9 mg) was dissolved in water (2 mL), and the solution was cooled with ice. To this was added triethylamine (9.2 μL), subsequently, 7-Hydroxycoumarin-3-carboxylic acid N-succinimidyl ester (20 mg) and dimethylformamide (2 mL) were added, and the mixture was stirred at room temperature for 3 hours. A 1% acetic acid aqueous solution (4 mL) was added and the solution was allowed to stand still overnight. The solution was allowed to pass through a membrane filter, and washed with a 1% acetic acid aqueous solution. The filtrate and the washing solution were combined and purified by HPLC. The intended fractions were collected and freeze dried.

Yielded amount: 10.6 mg

Yielded: 44%

$^1$H-NMR (400 MHz, deuterated water, ppm):

δ8.58 (s×2, 1H, Ar), δ7.53-δ7.56 (m, 1H, Ar), δ6.79 (m, 1H, Ar), δ6.67 (m, 1H, Ar), δ5.24 (d, 0.7H, J=3.7 Hz, H-1α), δ4.84 (d, 0.3H, J=8.2 Hz, H-1β), δ3.41-δ4.06 (m, 6H, H-2, H-3, H-4, H-5, H-6, H-6).

ESI-MS: calcd for C$_{16}$H$_{18}$NO$_9$ [M+H]$^+$ 368.10. found 368.1.

Maximum excitation wavelength: 402 nm

Maximum emission wavelength: 447 nm

Synthesis of 2-MCDG (2-Deoxy-2-(2-(7-methoxy-coumarin-4-yl) acetamido)-D-glucose)

2-MCDG represented by the following formula was synthesized as described below.

[Chemical formula 11]

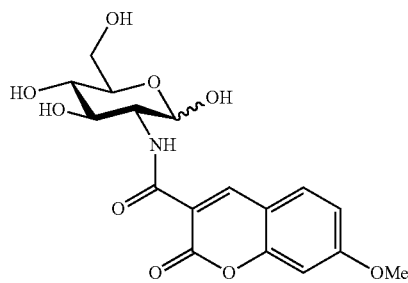

D-glucosamine hydrochloride (216 mg) was dissolved in water (1 mL), and dimethylformamide (9 mL) was added to this. To this were added MocAc—OH (234 mg) and HOBt (135 mg) and the mixture was cooled with ice. To this was added WSCD (187 µL), and the mixture was stirred at 0° C. for 1 hour. WSCD (33.9 µL) was additionally added and the mixture was further stirred for 2 hours, then, the neutral reaction solution was concentrated under reduced pressure, to the resultant residue was added water and the mixture was freeze dried. The residue was purified by HPLC. The intended fractions were collected and freeze dried.

Yielded amount: 69.6 mg

Yielded: 18%

$^1$H-NMR (400 MHz, deuterated methanol, ppm):

δ7.66 (m, 1H, Ar), δ6.85 (m, 2H, Ar), δ6.23 (s×2, 1H, Ar), δ5.03 (d, 0.6H, J=3.2 Hz, H-1α), δ4.54 (d, 0.4H, J=7.3 Hz, H-1β), δ3.26-δ3.81 (m, 9H, H-2, H-3, H-4, H-5, H-6, H-6, OMe).

ESI-MS: calcd for $C_{18}H_{22}NO_9$ $[M+H]^+$ 396.13. found 396.1.

Maximum excitation wavelength: 325 nm

Maximum emission wavelength: 392 nm

Example 2: Application of 2-PBDG to Acutely Dissociated Normal Neuron

This was conducted according to a method described in WO 2010/16587. The results are shown in FIG. 1.

Living neurons were acutely dissociated from mouse midbrain substantia nigra pars reticulata, and to which a mixed solution containing 100 µM of 2-PBDG and 20 µM of 2-TRLG was administered at 37° C. for 5 minutes. FIGS. 1A to C represent confocal microscopic images taken immediately before this. A is a fluorescence image in blue wavelength region (Blue channel, wavelength range: 415-580 nm). The position of cells is recognized by autofluorescence. The fluorescence signal intensity is represented by pseudo-color. B is a fluorescence image in red wavelength region (Red channel, 580-740 nm). A and B were obtained both by simultaneous excitation using 405 nm Blue diode laser at an intensity of 60%, wherein photomultipliers (PMT) 1 and 2 were used respectively, and the detection sensitivity of PMT2 was raised higher than PMT1 so that the presence or absence of invasion of 2-TRLG can be detected in a sensitive manner. C is a view in which the bright field image is overlaid on the fluorescence images of A and B.

FIGS. 1D to F represent images 4 minutes after initiation of washout of the administered solution after completion of administration of the fluorescence mixed solution. The image acquisition conditions are the same as for A to C. In Blue channel in D, it was confirmed that the intracellular fluorescence intensity was increased excepting nucleus as compared with that before administration (A). A dark part at the central region represents the nucleus of the cell. In contrast, the fluorescence intensity in Red channel did not increase as shown in E (green points are fluorescence signals transiently recognized on the cell surface represented by pseudocolor). 2-TRLG is a red fluorescence L-glucose derivative having a relatively large fluorescent group in the molecule, and no invasion of 2-TRLG into a cell teaches that the increase in fluorescence intensity observed in Blue channel is not caused by a loss of the plasma membrane integrity permitting passage of 2-TRLG.

Images 8 minutes after and 20 minutes after initiation of washout are shown in FIGS. 1G to I and FIGS. 1J to L, respectively. It was confirmed that 2-PBDG once taken up into a cell was not easily diminished.

Example 3: Application of 2-PBLG to Acutely Dissociated Normal Neurons

Figure 2:
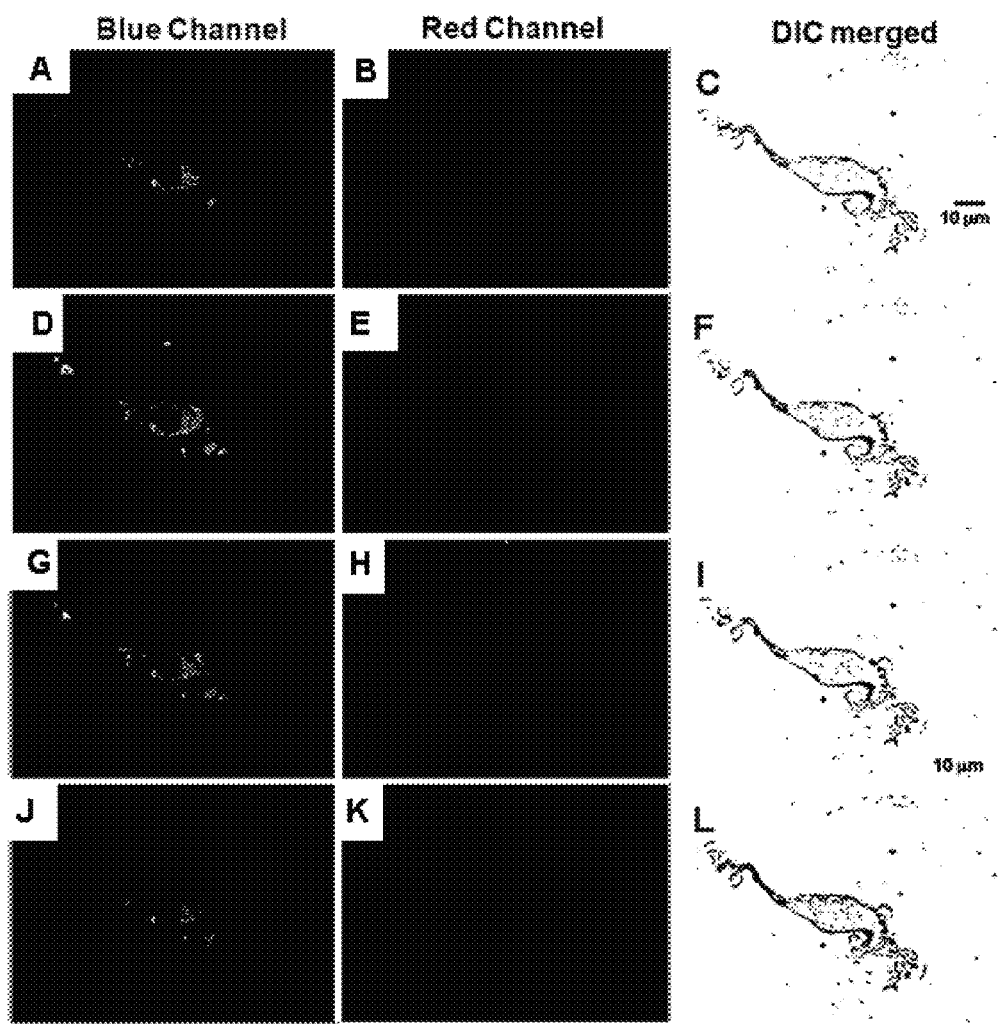
FIGS. 2A-2L show the results of administration of a mixed solution of an L-glucose derivative (2-PBLG: 100 µM) emitting blue fluorescence and an L-glucose derivative (2-TRLG: 20 µM) emitting red fluorescence to normal neurons.

An experiment was conducted in the same manner as in Example 2. The results are shown in FIG. 2.

FIGS. 2A to C represent confocal microscopic images immediately before administration of a mixed solution containing 100 µM of 2-PBLG and 20 µM of 2-TRLG at 37° C. to acutely dissociated neurons of mouse midbrain substantia nigra pars reticulata for 5 minutes.

Images 4 minutes after initiation of washout of the administered solution after completion of administration of the fluorescent mixed solution are shown in FIGS. 2D to F. The image acquisition conditions are the same as for A to C. In Blue channel in D, the intracellular fluorescence intensity scarcely increased as compared with that before administration (A). Also the fluorescence intensity of Red channel in E scarcely increased, and a loss of the plasma membrane integrity permitting invasion of 2-TRLG was not observed. FIGS. 2G to I and FIGS. 2J to L are images 8 minutes after and 20 minutes after initiation of washout, respectively. The slight increase in the fluorescence intensity recognized in a cell in D recovered to the autofluorescence level in J 20 minutes after initiation of washout. Thus, it is understood that 2-PBLG as an L-form glucose derivative is scarcely taken up into a cell, as compared with the result (FIG. 1) of administration of 2-PBDG as a D-form glucose derivative.

Comparative Example 1: Application of 2-HCDG to Acutely Dissociated Normal Neurons An experiment was conducted in the same manner as in Example 2. The results are shown in FIG. 3.

Figure 3:
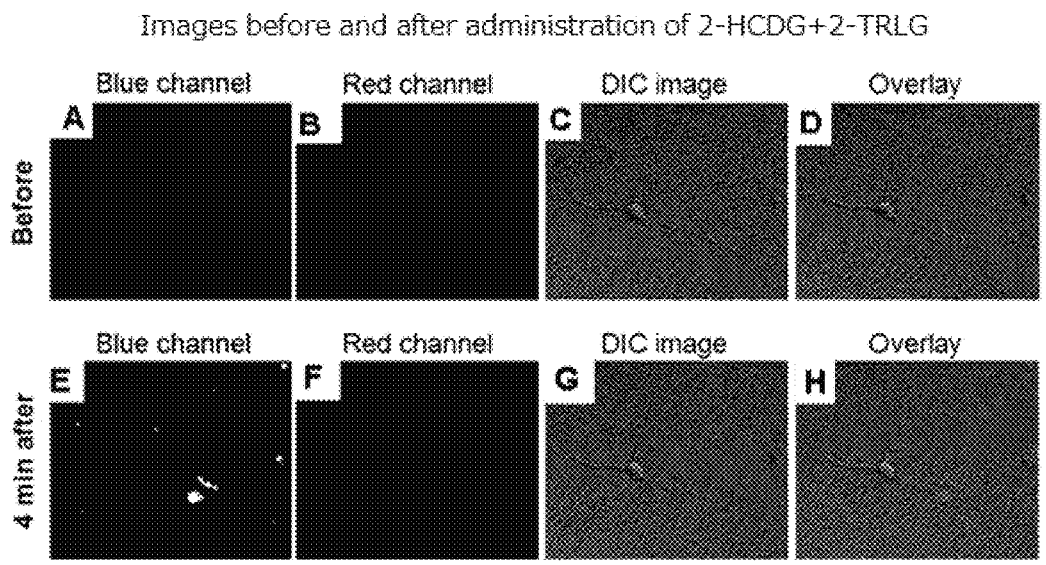
FIGS. 3A-3H show the results of administration of a mixed solution of a D-glucose derivative (2-HCDG: 100 µM) emitting blue fluorescence and an L-glucose derivative (2-TRLG: 20 µM) emitting red fluorescence to normal neurons.

FIG. 3 represents confocal microscopic images before and after administration of a mixed solution containing 100 µM of 2-HCDG and 20 µM of 2-TRLG at 37° C. for 3 minutes to neurons acutely dissociated from mouse midbrain substantia nigra pars reticulata. A and B are fluorescence images acquired before administration in Blue channel (415-580 nm) and Red channel (580-740 nm), respectively. The excitation wavelength is 405 nm. C is an image of differential interference (Differential Interference contrast, DIC). D is an overlay of the above-described images. E to H are the same as A to D, excepting that E to H are images acquired 4 minutes after initiation of washout of the fluorescence tracer solution after administration of the 2-HCDG+2-TRLG fluorescence tracer solution at 37° C. for 3 minutes. As observed in E and F, the blue fluorescence intensity of cell debris increases after administration, whereas no increase in the fluorescence intensity is detected before and after administration at the site where the neuron exists. Since invasion of 2-TRLG into a cell is not observed, the plasma membrane of the neuron is thought to be maintained intactly.

Comparative Example 2: Application of 2-MCDG to Acutely Dissociated Normal Neurons A mixed solution containing 100 μM of 2-MCDG and 20 μM of 2-TRLG was administered in the same manner as in Comparative Example 1 to neurons acutely dissociated from mouse midbrain substantia nigra pars reticulata, and an increase in the fluorescence intensity in the neurons before and after administration was not recognized.

Since the optimal excitation wavelength was as very low as 320 nm in this experiment, an image was acquired by Retiga-2000R CCD camera manufactured by Q-imaging via a custom-order filter constituted of an excitation filter (320 nm) (half width: 40 nm), a fluorescence filter (435 nm) (half width: 40 nm) and a dichroic mirror (409 nm), by a xenon lamp, using Nikon Ti-E real time deconvolution microscope.

Example 4: Uptake of 2-PBDG (100 μM) and 2-PBLG (100 μM) into Mouse Insulinoma Cell (MIN6) and Influence of Phloretin as a Glucose Transport Inhibitor (Experiment Method)
(1-1) Culture of Cell
Cryopreserved MIN6 cells (cells donated from Professor Miyazaki Junichi of Osaka University and cultured 5 to 8 passages) were subjected to culture according to an ordinary method, and cultures at 7 to 9 passages were used in experiments.
(1-2) Composition of Culture Solution Used for Culture of MIN6 Cell
High glucose-containing Dulbecco's modified Eagle's Medium (DMEM-HG) (SIGMA #D5648) (13.4 g), $NaHCO_3$ (Wako, No. 191-01305) (3.4 g) and 2-Mercaptoethanol (Wako, No. 135-14352) (5 μL) were dissolved in 1 liter of ultra-pure water (Mili Q), and pH was adjusted to 7.3 to 7.35 in a $CO_2$ incubator at 37° C. Hyclone Fetal Bovine Serum (Cat #SH30070.03) was added so as to give a final concentration of 10% and penicillin-streptomycin (Gibco #15140) was added so as to give a final concentration of 0.5%.
(1-3) KRB Solution
For measurement, a KRB solution having the following composition was used.
NaCl 129.0 mM, KCl 4.75 mM, $KH_2PO_4$ 1.19 mM, $MgSO_4 \cdot 7H_2O$ 1.19 mM, $CaCl_2 \cdot 2H_2O$ 1.0 mM, $NaHCO_3$ 5.02 mM, D-Glucose 5.6 mM, HEPES 10 mM (pH was adjusted to 7.35 with 1M NaOH). For inhibiting entrance and elimination of a fluorescently labeled glucose via gap junction/hemichannel, 0.1 mM Carbenoxolone (SIGMA #C4790) was added. This KRB solution was used as a solution for preparing a 2-PBLG solution.

(2) Preparation of 2-PBLG Solution and Other Fluorescent Sugar Derivative Solution
Preparation of 2-PBLG Solution
The total amount of a 0.5 mg 2-PBLG in a vial was recovered using a total amount of 30 μL of dimethyl sulfoxide (DMSO), and dissolved by adding it to 3.1 mL of a KRB solution by a method according to Yamada K. et al., Nat. Protoc. 2, 753-762, 2007.
Preparation of 2-PBDG Solution
The same procedure was conducted using 2-PBLG instead of 2-PBDG.
Preparation of PB—$NH_2$ Solution
The total amount of a 0.3 mg PB—$NH_2$ in a vial was dissolved in 3.1 mL of a KRB solution in the same manner, to obtain a PB—$NH_2$ solution having a final concentration of 200 μM.
Preparation of 2-NBDLG Solution
The total amount of a 0.5 mg 2-NBDLG in a vial was dissolved in 7.3 mL of a KRB solution, to obtain a 2-NBDLG solution having a final concentration of 200 μM.
Preparation of 2-PBDM Solution
The total amount of a 0.5 mg 2-PBDM in a vial was dissolved in 3.1 mL of a KRB solution according to preparation of the 2-PBLG solution, to obtain a 2-PBDM solution having a final concentration of 100 μM.
(3) Fluorescence Measurement
2-PBDG and 2-PBLG were charged into wells at the third column and the fifth column, respectively, using a 8-channel pipette. Before administration, the autofluorescence of each well was measured beforehand by a fluorescent micro plate reader (Flex Station, manufactured by Molecular Device). The measurement conditions include Bottom Read, Ex 401 nm, Em 453 nm, Cut off 420 nm, Averaging 3, and high sensitivity of Photomultiplier. In the measurement method, Well Scan Mode was used. In Well Scan Mode, the inside of one well was divided into 9 regions of interest (diameter: 1.5 mm) and measurement was performed each independently.
Next, in wells (3C, 3E, 3G) for measuring the effect of a glucose transport inhibitor phloretin, phloretin (final 150 μM) was administered beforehand from 5 minutes prior to administration of 2-PBDG, while KRB was added to other wells (3B, 3D, 3F). Similar operation was also conducted on the fifth column where 2-PBLG was to be administered. 2-PBDG and 2-PBLG were administrated at 37° C. for 10 minutes.
After completion of administration, a diluting operation of the fluorescence solution in the well using 300 μL of a KRB solution was repeated set times each for 30 seconds. The repetition time was determined so that the fluorescence intensity detected by wells of A-th row and H-th row set as a control group was equivalent to the fluorescence intensity of a blank well containing no cell, and complete washout was confirmed in every experiment. In the case of 2-PBDG and 2-PBLG, this washout process needed 8 minutes, thus, measurement of fluorescence after administration was carried out 9 minutes after.
According to this method, even if cells having undergone a loss of the plasma membrane contacted 2-PBDG and 2-PBLG and once took up these compounds into themselves, it is judged that contribution of the increase in the fluorescence intensity to the whole observation area was ignorable level since these compounds had already been washed out of the cells when performing the measurement. This was supported by a pharmacological inhibition experiment separately in which the increase in the fluorescence intensity almost completely disappeared in the presence of an inhibitor. The above-described method was conducted in the same manner also when other inhibitor, for example, cytochalasin B (10 μM) was added.

Figure 4:
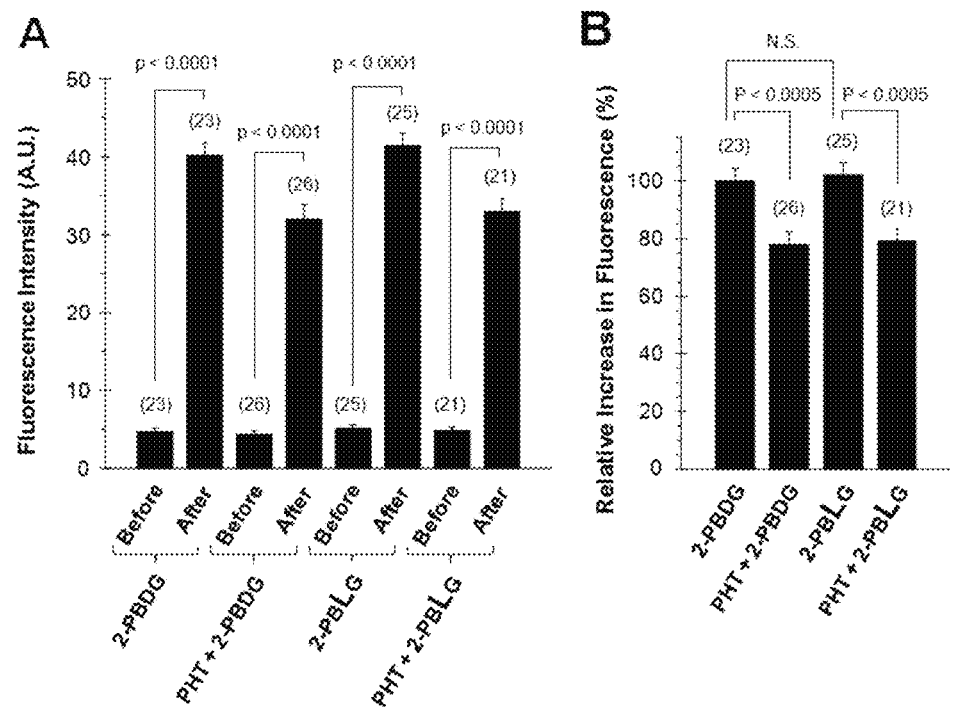
FIGS. 4A and 4B show the results, where a difference was quantitatively analyzed by a fluorescent microplate reader depending on the presence or absence of a glucose transport inhibitor phloretin when 2-PBDG (100 µM) and 2-PBLG (100 µM) are taken up into mouse insulinoma cells (MIN6) each for 5 minutes.

The results are shown in FIG. 4.

(Result of Experiment)

The results of administration of 2-PBDG obtained by linking Pacific Blue as a coumarin derivative to D-glucosamine and 2-PBLG obtained by linking Pacific Blue to L-glucosamine each at a concentration of 100 μM to a large number of MIN6 mouse insulinoma cells on day 10 after initiation of culture are shown in FIG. 4. The inhibition effect by 150 μM of phloretin (PHT) as a glucose transport inhibitor is shown as well. FIG. 4A shows the results of measurement of fluorescence intensity before and after administration by a fluorescent micro plate reader. The number in parentheses is the number of observation regions. Fluorescence before administration shows the autofluorescence of a cell. In all cases, fluorescence intensity increases significantly as compared with that before administration (ANOVA, Bonferroni-Dunn post hoc test). The excitation wavelength and the fluorescence wavelength were 401 nm and 453 nm, respectively. FIG. 4B shows a difference in fluorescence intensity before and after administration in A. The change in the fluorescence intensity when 2-PBDG is administrated in the absence of phloretin is expressed as 100%. There was no significant difference recognized between the fluorescence intensity of 2-PBDG and the fluorescence intensity of 2-PBLG. In the presence of phloretin, although a decrease in the fluorescence intensity was recognized in any of the case of 2-PBDG and the case of 2-PBLG, as compare with the absence of phloretin, most of the fluorescence was not inhibited by phloretin. The same result was also obtained in two experiments carried out independently, and the decreased values for 2-PBDG and 2-PBLG owing to phloretin were only 22.4% and 20.0% on average.

Figure 5:
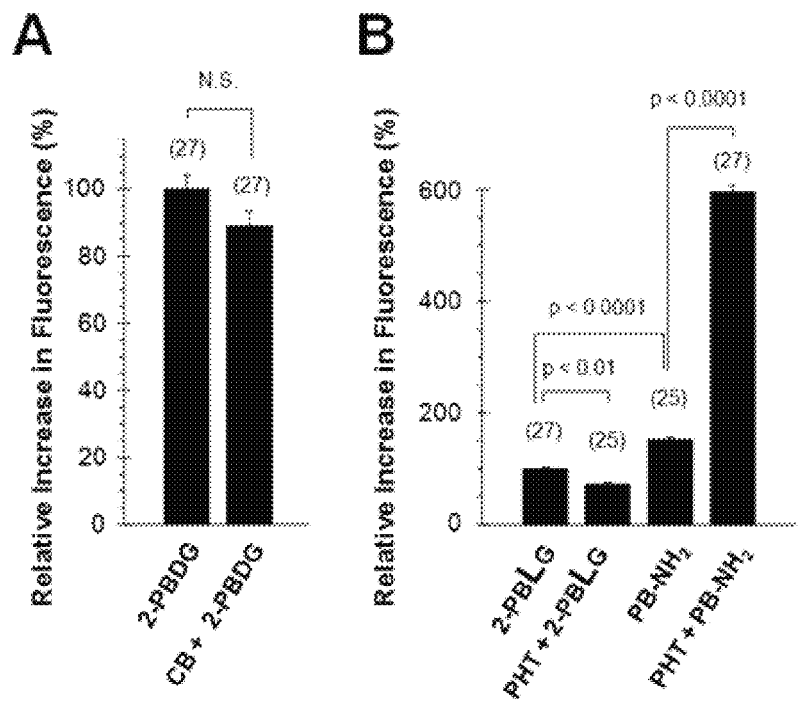
FIGS. 5A and 5B show the change in the fluorescence intensity by administration of a D-glucose derivative (2-PBDG), an L-glucose derivative (2-PBLG) and PB-NH$_2$ as a basic structure of a non-sugar portion to mouse insulinoma cells (MIN6) on day 10 of culture, and the effect by a glucose transport inhibitor.

Example 5: Change of Fluorescence Intensity by Administration of 2-PBDG, 2-PBLG and PB—$NH_2$ and Effect by Glucose Transport Inhibitor The change of fluorescence intensity by administration of a D-glucose derivative (2-PBDG), an L-glucose derivative (2-PBLG) and PB—$NH_2$ prepared by amidating Pacific Blue (PB) chromophore group to MIN6 cells on day 10 of culture and the effect by a glucose transport inhibitor were confirmed in the same manner as in Example 4. PB—$NH_2$ has the following structure (Ex max. 402 nm, Em max. 451 nm). The results are shown in FIG. 5.

[Chemical formula 12]

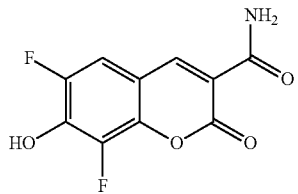

(Result of Experiment)

As is understood from FIG. 5A, the GLUT selective inhibitor cytochalasin B (CB, 10 μM) did not show a significant inhibitory effect to an increase in the fluorescence intensity by administration of 2-PBDG (100 μM). In this example, the average fluorescence intensity was decreased in the presence of CB as compared with that in the absence of CB, however, there was a case when an increase was detected among the results of experiments carried out 3 times independently, thus, the results were not constant. FIG. 5B shows the effect of a glucose transport inhibitor phloretin (PHT, 150 μM) on the increase in fluorescence intensity by administration of 2-PBLG (100 μM) or PB—$NH_2$ (100 μM). Phloretin inhibited the increase in the fluorescence intensity by 2-PBLG slightly like in FIG. 4, but adversely, remarkably promoted the increase in the fluorescence intensity by PB—$NH_2$. It is to be noted that the unit of the longitudinal axis of B is different from A. The experiments of administration for 2-PBLG and PB—$NH_2$ were carried out simultaneously on the same culture plate, and a remarkable enhancement effect by phloretin on PB—$NH_2$ response was detected in any of three experiments carried out independently, and the increase in the fluorescence reached an average value of 384.1±24.2% (n=3) compared to when only PB—$NH_2$ is administrated. PB—$NH_2$ having no sugar structure showed an increase in the fluorescence intensity significantly larger than that of an L-glucose derivative 2-PBLG having a sugar structure.

Figure 6:
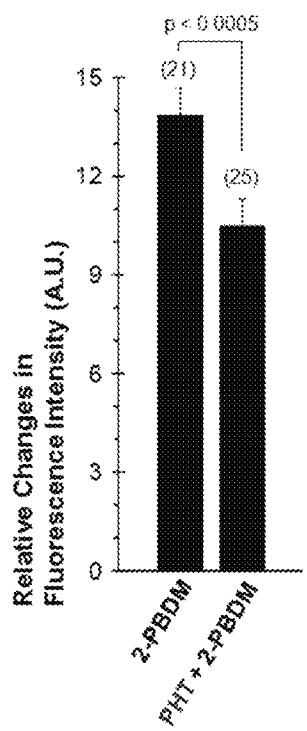
FIG. 6 shows the results, where a difference was quantitatively analyzed by a fluorescent microplate reader depending on the presence or absence of a glucose transport inhibitor phloretin when 2-PBDM (100 µM) is taken up into mouse insulinoma cells (MIN6) for 5 minutes.

Example 6: Administration of 2-PBDM (100 μM) to Mouse Insulinoma Cell (MIN6), and Influence of Phloretin as a Glucose Transport Inhibitor An experiment was conducted in the same manner as in Example 4. The results are shown in FIG. 6.

2-PBDM (100 μM) was administered to MIN6 cells (20000 cells/well) on day 10 of culture (10 DIV) and the inhibition effect by phloretin (150 μM, PHT) on the increase in fluorescence intensity before and after administration was measured by FlexStation, and it was confirmed that phloretin had a slight but significant inhibitory effect in case of 2-PBDM. The experiment was carried out 3 times independently, and the same results were obtained in all cases. In the experiment of administration of 2-PBDM, excitation occurred at a maximum excitation light wavelength of 404 nm and fluorescence was acquired at a maximum emission wavelength of 453 nm.

Example 7: Imaging of Tumor Cell Cluster Composed of Mouse Insulinoma Cell (MIN6) Using 2-PBDG or 2-PBLG (2-PBDG/2-TRLG or 2-PBLG/2-TRLG or 2-PBLG/2-NBDLG/2-TRLG was Used)

(Experiment Method)
(1) Preparation of Mouse Insulinoma Cell (MIN6)

A culture solution prepared by suspending MIN6 cells at a proportion of $10 \times 10^4$ cells/mL was dropped in an amount of 10 μL on a glass cover slip, then, allowed to adhere to the glass surface, and 3 mL of the culture solution was added and cultured. The half quantity of the culture solution was changed every three days.

(1-1) Culture of MIN6 Cell

Cryopreserved MIN6 cells (cells donated from Professor Miyazaki Junichi of Osaka University and cultured 5 to 8 passages) were subjected to culture according to an ordinary method, and cultured 7 to 9 passages which were used in experiments. The half amount of the culture solution was changed every two days.

(1-2) Composition of Culture Solution Used for Culture of MIN6 Cell

High glucose-containing Dulbecco's modified Eagle's Medium (DMEM-HG) (SIGMA #D5648) (13.4 g), $NaHCO_3$ (Wako, No. 191-01305) (3.4 g) and 2-Mercaptoethanol (Wako, No. 135-14352) (5 μL) were dissolved in 1 liter of ultra-pure water (Mili Q), and pH was adjusted to 7.3 to 7.35 in a $CO_2$ incubator at 37° C. Hyclone Fetal Bovine Serum (Cat #SH30070.03) was added so as to give a final concentration of 10% and penicillin-streptomycin (Gibco #15140) was added so as to give a final concentration of 0.5%.

(1-3) Culture Solution Prepared by Suspending MIN6 Cell at Proportion of $10 \times 10^4$ Cells/mL MIN6 cells were prepared by using a culture solution so that the number of cells was $10 \times 10^4$ cells/mL.

(2) Preparation of 2-PBLG Solution and Mixed Solution with Other Fluorescent Sugar Derivative Preparation of 2-PBLG Solution The total amount of a 0.5 mg 2-PBLG in a vial was recovered using a total amount of 30 μL of dimethyl sulfoxide (DMSO), and dissolved by adding it to 6.25 mL of a HEPES solution for acquiring image by a method according to Yamada K. et al., Nat. Protoc. 2, 753-762, 2007.

Preparation of 2-PBDG Solution

The same procedure was conducted using 2-PBLG instead of 2-PBDG.

Preparation of 2-NBDLG Solution

The total amount of a 0.5 mg 2-NBDLG in a vial was dissolved in 14.6 mL of a HEPES solution for acquiring image, to obtain a 2-NBDLG solution having a final concentration of 100 μM.

Preparation of 2-TRLG Solution

The total amount of a 0.2 mg 2-TRLG in a vial was recovered using a total amount of 100 μL of DMSO. It was dissolved by adding it to 6.5 mL of a KRB solution.

Preparation of 2-PBLG+2-TRLG Mixed Solution

The above-described 2-PBLG solution and the 2-TRLG solution were mixed at 1:1, to prepare the intended fluorescent derivative mixed solution.

(2-1) HEPES Solution for Acquiring Image

A solution having the following composition which is the same as that of the KRB solution used in the FlexStation experiment was used.

NaCl 120.0 mM, KCl 4.75 mM, $KH_2PO_4$ 1.19 mM, $MgSO_4 \cdot 7H_2O$ 1.19 mM, $CaCl_2 \cdot 2H_2O$ 1 mM, $NaHCO_3$ 5.02 mM, D-Glucose 5.6 mM, HEPES 10 mM (adjusted to pH 7.35 with 1M NaOH). For inhibiting entrance and elimination of fluorescently labeled glucose via a gap junction/hemichannel, 0.1 mM Carbenoxolone (SIGMA #C4790) was added. The HEPES solution for image acquisition was used as a solution for preparing a 2-PBLG solution and as a solution for preparing a 2-PBLG/2-TRLG solution and 2-PBLG/2-NBDLG/2-TRLG solution.

(3) Administration of DAPI Solution to MIN6 Cells

A glass cover slip to which MIN6 cells had been adhered and wherein MIN6 cells had been cultured for 10 to 13 days was transferred into a DAPI solution containing 5.6 mM D-glucose filled in a 35 mm dish, and allowed to stay for 45 minutes to 1 hour while warming at 37° C. to allow cells to take up DAPI. In a separate experiment, DAPI was administered while continuously observing on a confocal microscope, and it was confirmed that the morphological change of the cell due to DAPI administration and irradiation with 405 nm laser was not recognized during the experimental period.

Preparation of DAPI solution: 4',6-Diamidino-2-phenylindole DAPI (No. 049-18801, Wako Pure Chemical Industries, Osaka) was diluted with a HEPES solution for image acquisition so to be at the final concentration of 1 μg/mL, and used.

(4) Method of Fixing Glass Cover Slip, Wherein MIN6 Cells have been Cultured, into Perfusion Chamber for Fluorescence Measurement by Using Metal Guide A glass cover slip wherein MIN6 cells had been cultured was transferred into a HEPES solution for image acquisition in a perfusion chamber set on a universal stage (Leica 11600234) on a confocal laser scanning microscope (TCS SP5 available from Leica), and adhered gently and tightly to the glass surface at the bottom of the chamber. After allowing to stand still, the both sides of the cover slip were held and carefully pressed by two rectangular metal guides (length: 10 mm, width: 2 mm, thickness: 0.7 mm, made of silver) in parallel to the long axis of the cover slip from the right and left sides thereof, so that the cover slip did not move even in the flow. Further, there is an excellent effect that in the space sandwiched by the metal guides, the perfusion solution flows smoothly as a laminar flow and quick solution exchange is possible.

(4-1) Perfusion Chamber for Fluorescence Measurement on Confocal Laser Scanning Microscope Stage On an aluminous warming control platform having a round hole (diameter: 18 mm) at the bottom for an objective lens (PH1, Warner Instruments, USA, warmed at 37° C. by a temperature control apparatus TC-324, Warner Instruments), a cover glass (width: 24 mm×length: 50 mm, thickness: No. 1, Warner Instruments, No. CS-24/50) was closely adhered to parts other than the round hole at the center of the platform using a silicon grease (HIVAC-G, Shin-Etsu Silicone, Tokyo). Then, on the cover glass, a silicon plate having a thickness of 1 mm (width: 20 mm×length: 50 mm) on which opening in the form of streamline had been made at the center (at the side in contact with the glass bottom, width: 10 mm×length: 35 mm, curvature radius: 33 mm, and at the side not in contact with the glass surface, namely, at the upper side, the size is slightly wider) was placed, and adhered closely to the cover glass without using a silicon grease.

At the upstream corner of the streamline-shaped hole on the silicon plate, a 20 gauge Cattelan needle having a blunt tip was set and used as an inlet.

As a stainless tube for removing a perfusion solution (outlet), a tube having a tip crushed flatly and cut obliquely according to a method described in non-patent document 16 was used, and in vacuum suction, both air and a solution were sucked simultaneously to attain stabilization.

(5) System of Feeding Perfusion Solution to Perfusion Chamber (a) Warming of Perfusion Solution and Feeding Thereof to Perfusion Chamber A perfusion solution feeding system is equipped with one 60 mL cylinder for a control solution and five 10 mL cylinders for agent feeding, which can be switched as needed by a magnetic valve to allow perfusion. In experiments according to the present invention, a 5.6 mM glucose-containing HEPES solution for image acquisition was administered using the 60 mL cylinder and a mixed solution of 2-PBLG/2-NBDLG/2-TRLG, a mixed solution of 2-PBDG/2-TRLG, or a mixed solution of 2-PBLG/2-TRLG was administered using one of the five 10 mL cylinders. As described below, to avoid generation of bubbles in the perfusion chamber, both the solutions were heated beforehand, combined in one tube before being introduced into the perfusion chamber, the flow rate thereof being controlled by a flow rate controller, then, heated again by an inline heater and fed to the perfusion chamber on the confocal microscope.

The HEPES solution for image acquisition was fed from the 60 mL cylinder warmed in an aluminum syringe heater (Model SW-61, temperature control unit is No. TC-324B, Warner Instruments) to a three-way stopcock for flushing the inside of a tube of a solution feeding line, subsequently, to the normally opened side of an ultra-compact magnetic valve (EXAK-3, 3 way clean valve, Takasago Electric, Nagoya) via a thin and lowered gas-permeability soft tube (PharMed tube, AY242409, Saint-Gobain Performance Plastics, Ohio). Opening and closing of the magnetic valve was controlled by a pulse generating apparatus (Master 8, manufactured by AMPI, Israel). The HEPES solution for image acquisition was fed continuously from a medium bottle into the 60 mL cylinder using a peristaltic pump (MCP pump, 12 rollers, Ismatec), and the solution feeding speed of the pump was controlled accurately to obtain the same value as the solution dropping speed so that the height of the upper surface of the solution in the cylinder did not change during the experiment. Since the solution feeding speed of the peristaltic pump is displayed digitally, if the speed of feeding the solution to the perfusion chamber changes during the experiment, it is immediately detected based on a change in the height of the solution surface. Since this solution is constantly renewed, a syringe heater SW-61 was set at 38.5° C. for maintaining the solution temperature.

On the other hand, the mixed solution of 2-PBLG and 2-TRLG, the mixed solution of 2-PBLG/2-NBDLG/2-TRLG and the like was fed from the 10 mL cylinder warmed at 37.5° C. set in a syringe heater (Model SW-6, temperature control unit is No. TC-324, Warner Instruments). The cylinder is connected via three-way stopcock to the normally closed side of a magnetic valve different from one for the HEPES solution for image acquisition, and switching to the control solution can be performed as needed by control of a pulse generating apparatus and the control solution can be fed. Six 10 mL cylinders can be set on the syringe heater SW-6, and distilled water was charged in one of them and a probe for monitoring the temperature of a heating block was inserted.

The HEPES solution for image acquisition as a control solution, and the mixed solution of 2-PBLG and 2-TRLG, the mixed solution of 2-PBLG/2-NBDLG/2-TRLG and the like were, after going out of the outlet of the magnetic valve, collected in one route by a compact manifold (MPP-6, Warner Instruments) having 6 ports. The outlet of the MPP-6 manifold was connected to a short PharMed tube, and this tube was inserted into a flow rate controller which can increase and decrease the aperture by a screw, and the flow rate was regulated as 1.2±0.2 mL/minute by controlling the aperture. This PharMed tube was connected to an inline heater (Multi-Line In-Line Solution Heater SHM-8, temperature control unit is TC-324B, Warner Instruments) in the shortest distance. It is because the temperature of the solution to be introduced into a perfusion chamber is warmed immediately before introduction. The temperature of the SHM-8 inline heater was so regulated that the actually measured temperature of a perfusion solution in the chamber was 36-37° C. in the region where the cover slip exists, according to the perfusion speed. The warmed solution was connected to a stainless pipe (inlet) placed upstream of the perfusion chamber in the shortest distance via a short Tygon tube (R-3603, inner diameter 1/32 inch) and fed to the perfusion chamber.

Since pressure of feeding a solution from a cylinder is determined by using hydrostatic pressure, a difference in height may generates a difference in perfusion speed, to cause a variation in the height of the water surface in a chamber. To avoid this, for a mixed solution of 2-PBLG and 2-TRLG, a mixed solution of 2-PBLG/2-NBDLG/2-TRLG and the like, solution feeding is not performed during an experiment in a single experiment, and after completion of each experiment, a solution was added so that the solution upper surface showed approximately the same height with a no-fluorescent glucose-containing HEPES solution, because the administration time of the solution is short. Further, by carefully controlling the length and the thickness of a tube connected to a cylinder so as to cause flow at the same speed as the perfusion speed of a HEPES solution for image acquisition as a control solution, a variation of the solution surface due to solution exchange can be avoided. After completion of the experiment and before starting thereof, the inside of a tube was flashed sufficiently to ensure smooth flow.

(b) Maintenance of Laminar Flow in Perfusion Chamber and Removal of Perfusion Solution A stainless tube (outlet) for removing a perfusion solution was introduced to two large glass traps in series by a Tygon tube, and calmly sucked by a vacuum pump (DAP-15, ULVAC KIKO, Inc.). The suction pressure was monitored by a pressure gauge installed in a line branched from a suction line in the middle of two large glass traps, and adjusted to 35 kPa by controlling the degree of opening and closing of a three-way stopcock.

For maintenance of a laminar flow in a perfusion chamber, first, a solution of a blue dye (Pontamine sky blue, diluted to a concentration of 1% or less in use) was dropped around an inlet, and the left-right symmetry, uniformity and reproducibility of flow were ensured.

For confirmation of the temperature of each part in a perfusion solution in a chamber, an ultrafine thermistor probe (IT-23 manufactured by Physitemp) was used (non-patent document 16). The tip of an outlet was observed by an operation microscope (POM-50II, KONAN MEDICAL, Nishinomiya) installed on a chamber and cleaned in every experiment, for preventing a variation of suction pressure due to attachment of a salt derived from a HEPES solution during the experiment.

(6) Image Acquisition Condition

A laser scan confocal microscope (manufactured by Leica, TCS-SP5 system, microscope body is DMI6000 CS trino electromotive inverted microscope) was used in conventional mode. Regarding laser used, a 405 nm diode laser was used for excitation of 2-PBLG and 2-PBDG, excitation of a mixed solution of 2-PBLG (or 2-PBDG) and 2-TRLG with a single light source, or live staining of nucleus by DAPI. The irradiation intensity was appropriately adjusted in accordance with the fluorescent pigment used so as to obtain sufficient observation intensity by an acoustic optical polarization element (Acoustic Optical Tunable Filter, AOTF). 2-NBDLG and 2-TRLG were excited by 488 nm Argon laser. The scan speed was 200 Hz or 400 Hz.

In fluorescence detection, a photomultiplier detector (PMT) 1 was used for detection of blue fluorescence by 2-PBDG or 2-PBLG and images were acquired in a wavelength detection range set at 415-580 nm in the case of detection of bicolor of 2-PBLG/2-TRLG and in a wavelength detection range set at 415-500 nm in the case of detection of tricolor of 2-PBLG/2-NBDLG/2-TRLG. For detection of green fluorescence by 2-NBDLG, PMT2 (called green channel, the same shall apply hereinafter) was used in a wavelength detection range of 500-580 nm. For detection of red fluorescence by 2-TRLG, PMT3 (called red channel, the same shall apply hereinafter) was used in a wavelength detection range of 580-740 nm. Selection of the wavelength range for detection of fluorescence of blue, green and red described above was carried out not by an emission filter mode usually used but by a mode combining prism spectrum and slit (Leica, standard of TCS-SP5). When 488 nm argon laser was used, a beam splitter of 500 nm (RSP500) was used. In the SP5 system, a beam splitter for 405 nm is one of 415 nm fixed mode independently from the above-described case. In excitation of fluorescence in the experiment of detection of tricolor of 2-PBLG/2-NBDLG/2-TRLG, firstly, images of 2-NBDLG (green) and 2-TRLG (red) by excitation at 488 nm were acquired, and immediately after, an image of 2-PBDLG (blue) was acquired by excitation at 405 nm in sequential mode. In the case of detection of bicolor of 2-PBLG/2-TRLG, images of 2-PBLG (blue) and 2-TRLG (red) were acquired simultaneously by single excitation of 405 nm diode laser under sensitivity condition wherein the detection sensitivity in the red wavelength region is higher than the detection sensitivity in the blue wavelength range (blue 617 V, red 738 V, and the like) so that invasion of 2-TRLG into a cell can be detected effectively.

In the acquisition of differential interference contrast (DIC) image for capturing the three-dimensional structural feature of a tumor cell cluster, one detected by a detector for transmitted light (PMT Trans, typical detection sensitivity: 145 to 200 V) simultaneously activated during excitation at 488 nm (or 405 nm) was used. For avoiding problems of the switching time and the switching shock when inserting a polarizer and an analyzer necessary for image acquisition of a differential interference mode (DIC) into an optical path, the polarizer and the analyzer for DIC were allowed to remain in the optical path even during the image acquisition by 405 nm excitation.

In this method, for obtaining high resolution for the xy axis and an angle of view to include the whole cell cluster in the field of view, an objective lens having high resolution, ×40 oil lens (HCX PL APO CS 40.0×1.25 OIL UV, NA1.25) was used with the aperture opened. For increasing the acquired fluorescence intensity, the pinhole size was set at 3 airy units. It was confirmed in the acquired image that nucleus and cytoplasm within the cell can be practically discriminated in the z-axis direction even with this pinhole size. The image was acquired at a depth of 12 bit, basically without using zoom (1×) at a number of pixels of 1024×1024 or 512×512.

The above-described solution administration and all image acquisition procedures were conducted in a dark room maintained at a constant temperature (24° C.) for 24 hours.

The results are shown in FIGS. 7 to 17.

(Result of Experiment)

Figure 7:
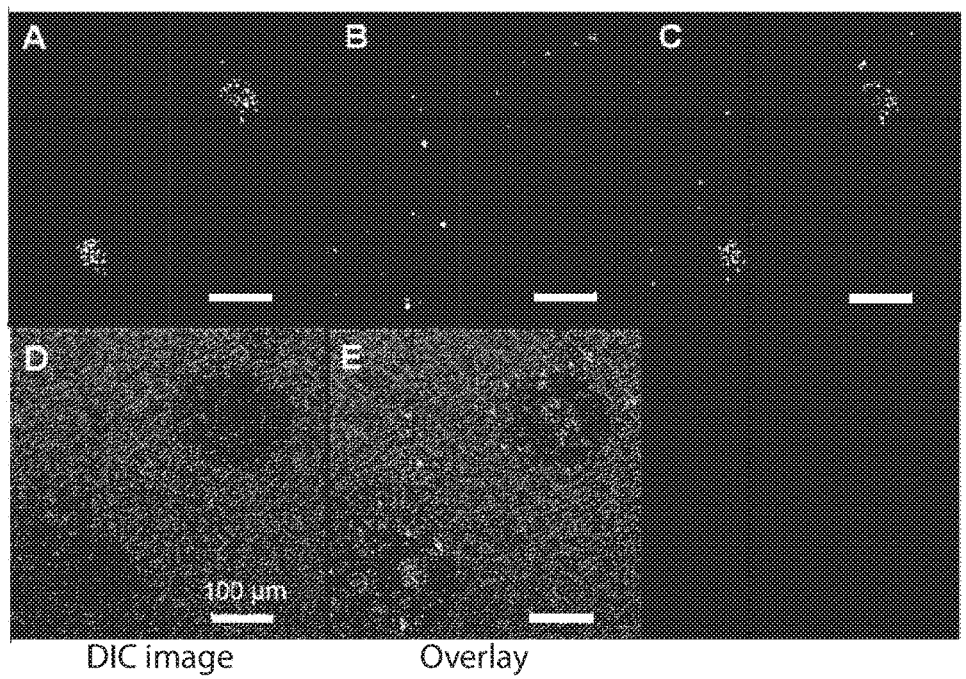
FIGS. 7A-7E are micrographs showing the spatial configuration of cells having undergone apoptosis, cells having undergone necrosis and cells having a cellular nucleus stained intensely with DAPI in a cancer cell cluster (spheroid, MIN6 cells on day 15 in culture) having shown three-dimensional development in culture.

In FIG. 7, spatial configuration of cells having undergone apoptosis, cells having undergone necrosis and cells having a cellular nucleus stained strongly with DAPI, in a cancer cell cluster revealing three-dimensional development under culture (spheroid, MIN6 cell on day 15 of culture), can be confirmed. In FIG. 7A, cells having a nucleus linking extremely strongly to 4',6-diamidino-2-phenylindole (DAPI) emitting blue fluorescence are present at the center of spheroid which has grown to have diameter over certain level (about 100 micron or more) and height over certain level (about 50 micron or more). DAPI is applied to living cells themselves not fixed with formalin. In FIG. 7B, cells having undergone apoptosis are visualized with green fluorescence by a live apoptosis marker pSIVA-IANBD (IM-GENEX, San Diego, USA). Positive cells are scattered around the periphery of spheroid. In FIG. 7C, red fluorescence indicates cells invaded by propidium iodide (PI) which is popular as a necrosis marker. It is understood that these cells are concentrated relatively around the center of spheroid. FIG. 7D shows a differential interference microscope image. FIG. 7E shows an overlaid image of them. Image acquisition was carried out according to the method for detection of tricolor of 2-PBLG/2-NBDLG/2-TRLG.

Figure 8:
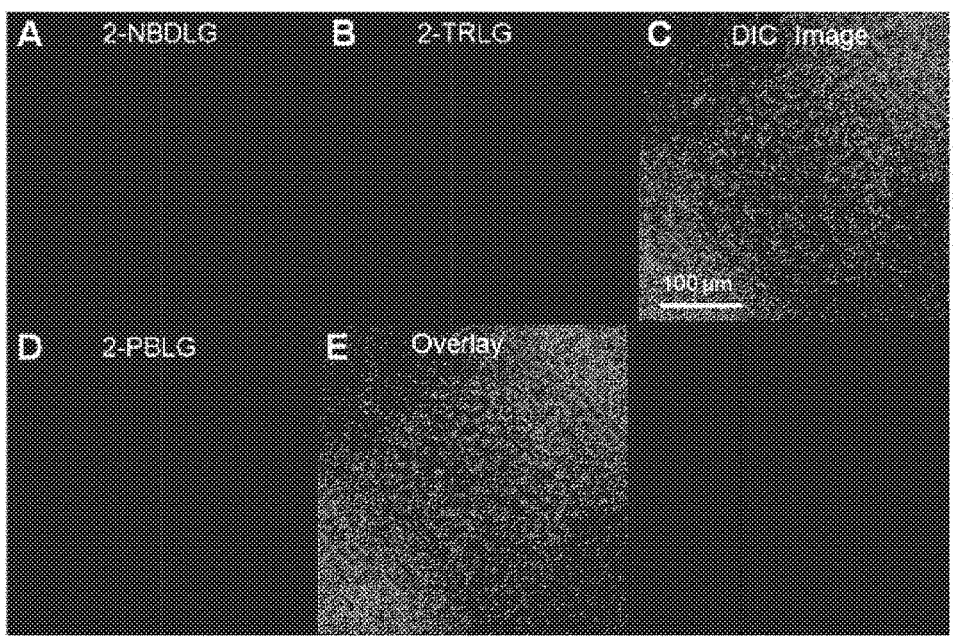
FIGS. 8A-8E are micrographs of a cell cluster (on day 13 from initiation of culture) formed by aggregating a lot of MIN6 cells.

FIG. 8 shows a micrograph of a cell cluster (on day 13 after initiation of culture) formed by aggregation of a lot of MIN6 cells. FIG. 8 is an image before administration of a fluorescently labeled glucose derivative mixed solution composed of 2-NBDLG, 2-TRLG and 2-PBLG. FIG. 8A and FIG. 8B are fluorescence images acquired simultaneously at wavelength ranges of 500-580 nm (green) and 580-740 nm (red) optimum for observation of 2-NBDLG and 2-TRLG, respectively, under excitation by 488 nm argon laser. FIG. 8C is a differential interference micrograph (Differential Interference Contrast, DIC) acquired simultaneously with A and B. FIG. 8D is a fluorescence acquisition image in the wavelength range of 415-580 nm (blue) obtained by sequential excitation by 405 nm diode laser, subsequently to scanning in A, B, C. FIG. 8E is an overlay of them. When compared with C, a pattern of slight autofluorescence is found.

FIG. 9 to FIG. 12 show the results of imaging using 2-PBLG of a tumor cell cluster composed of mouse insulinoma cells (MIN6). Images were acquired by a real time laser scanning confocal microscope using a mixed solution composed of 100 μM of 2-PBLG, 100 μM of 2-NBDLG and 20 μM of 2-TRLG.

Figure 9:
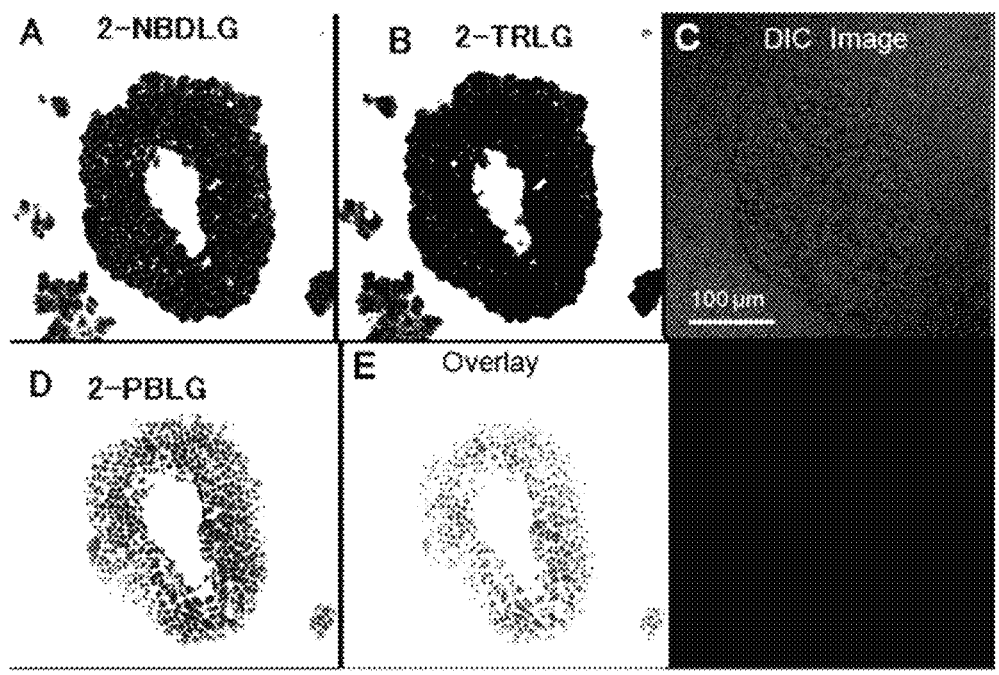
FIGS. 9A-9E are images acquired by a real time laser scanning confocal microscope during administration of a mixed solution composed of 100 µM of 2-PBLG, 100 µM of 2-NBDLG and 20 µM of 2-TRLG to a tumor cell cluster composed of mouse insulinoma cells (MIN6) in Example 7.

FIG. 9 shows fluorescence acquisition images of green (A), red (B) and blue (D) of a MIN6 cell cluster during administration of a mixed solution composed of 100 μM of 2-PBDLG, 100 μM of 2-NBDLG and 20 μM of 2-TRLG, a differential interference micrograph thereof (C), and an overlay (E) of them. Since a lot of cells at the center of the cell cluster have increased cell membrane permeability, there is a tendency that any fluorescently labeled glucose derivatives are taken up strongly into the cells during administration. When three colors of red, green and blue are overlaid, white color is obtained. Since images of A, B and C were acquired simultaneously over a period of several seconds before sequentially acquiring an image of D, a perfusion solution invades more deeply into the cell cluster in acquiring the image of D.

Figure 10:
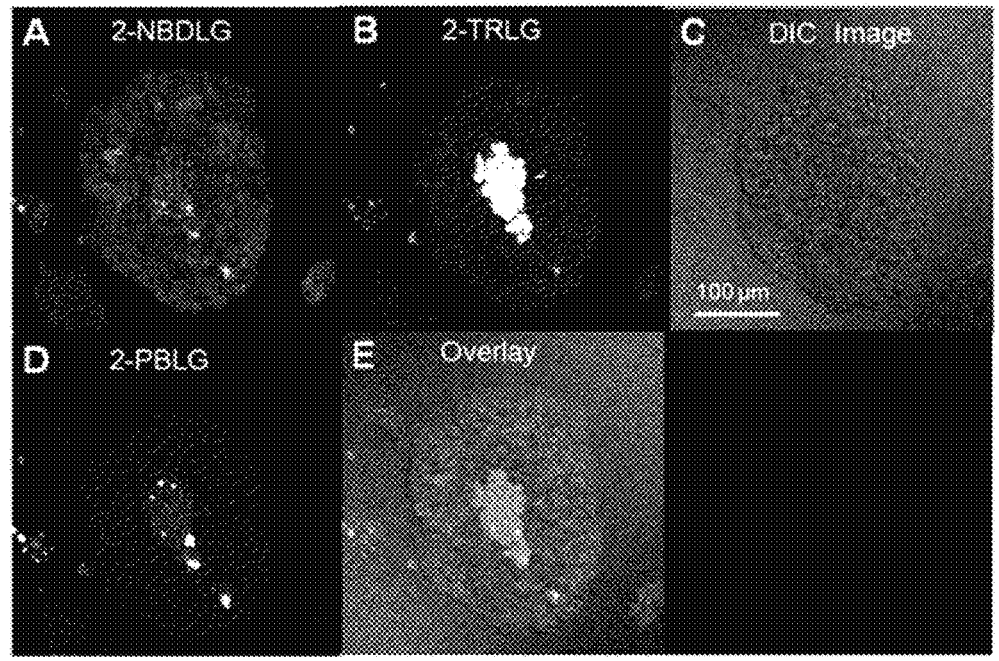
FIGS. 10A-10E are images acquired 2 minutes after completion of administration in Example 7.

FIG. 10 is equivalent to FIG. 9, excepting that FIG. 10 is an image at a time point of 2 minutes after completion of administration of a mixed solution of 2-NBDLG, 2-TRLG and 2-PBLG. The fluorescence intensity at the center of a cancer cell cluster tends to be more intense as a whole compared to the peripheral parts (A, B, C, D). When a fluorescence image by plasma membrane impermeable 2-TRLG is observed, it is found that cells appearing to have deteriorated membrane condition are scattered not only around the center of the cell cluster but also around the peripheral regions of the cell cluster (B). At a time point of 2 minutes after completion of administration of the mixed solution, such cells include also cells emitting green or blue fluorescence since 2-NBDLG and 2-PBLG are not completely washed out from the cells after 2-NBDLG and 2-PBLG once invade into the cells. Most of these cells lose intense fluorescence derived from 2-NBDLG (green) and 2-PBLG (blue) in several minutes after completion of administration of the mixed solution (see, 1).

Figure 11:
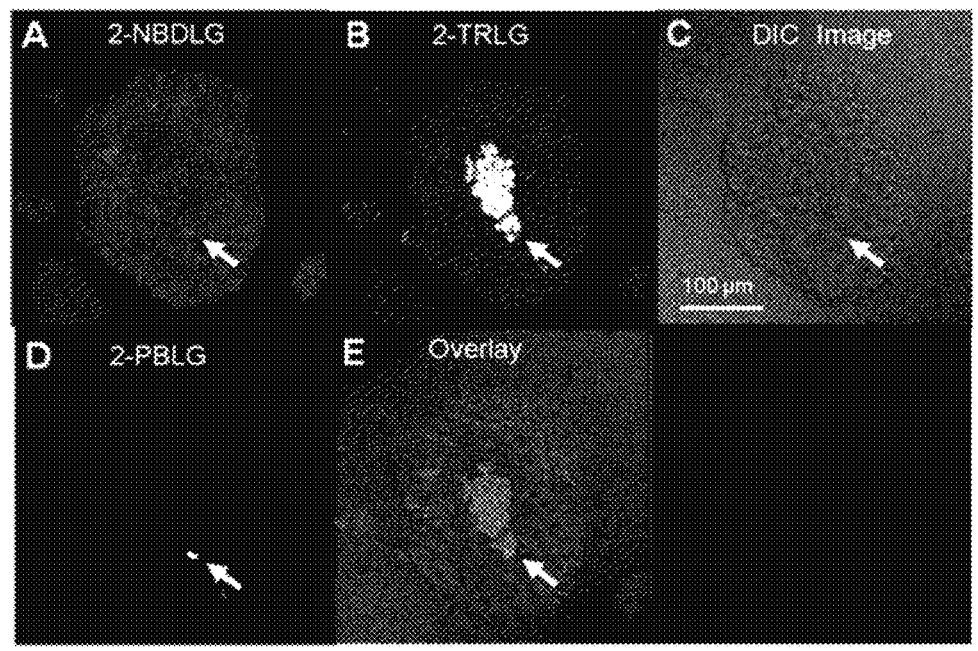
FIGS. 11A-11E are images acquired 8 minutes after completion of administration in Example 7.

FIG. 11 is an image at a time point of 8 minutes after completion of administration of a mixed solution. A and D show no tendency that the fluorescence intensity at the center of a cancer cell cluster is particularly intense in comparison with peripheral parts thereof. Regarding cells indicated by an arrow, however, intense blue fluorescence by 2-PBLG is maintained continuously. These cells show a tendency that also the fluorescence intensity by 2-NBDLG is more intense than peripheral cells, however, it is difficult to specify these cells only by the fluorescence imaging by 2-NBDLG (A). 2-TRLG has a nature that once taken up into a cell which is not completely dead but having increased membrane permeability, it does not easily flow out of the cell, and emits intense fluorescence. Therefore, such cells present in the hypoxic and low-nutrition region mainly at the center of a cancer cell cluster can be visualized and recognized, even 8 minutes after completion of administration (B). It is to be noted that cells showing intense blue fluorescence by 2-PBLG indicated by an arrow reveal very weak red fluorescence (B, E).

Figure 12:
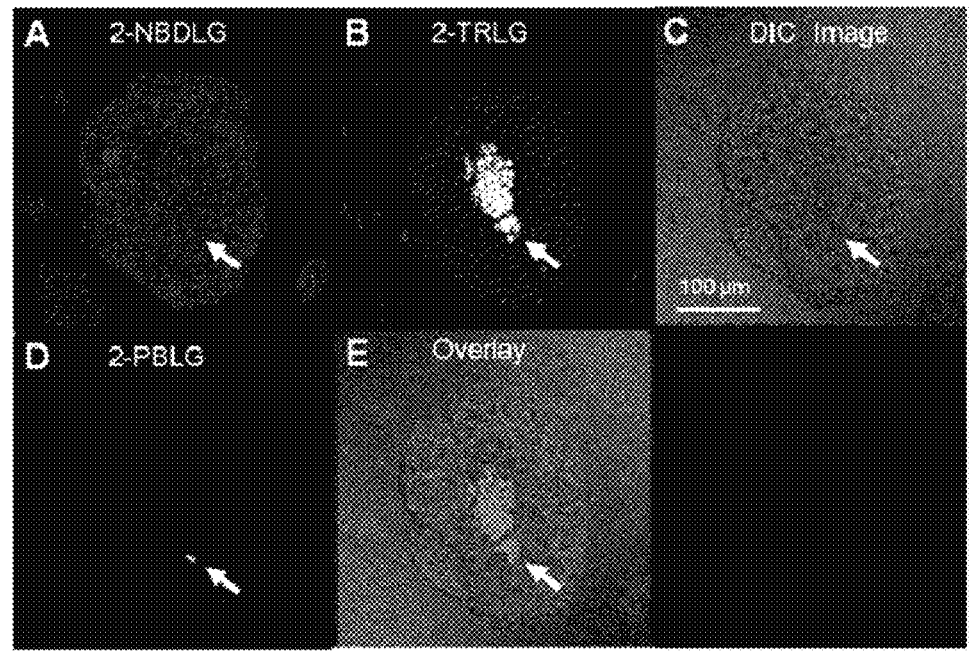
FIGS. 12A-12E are images acquired 12 minutes after completion of administration in Example 7.
Figure 13:
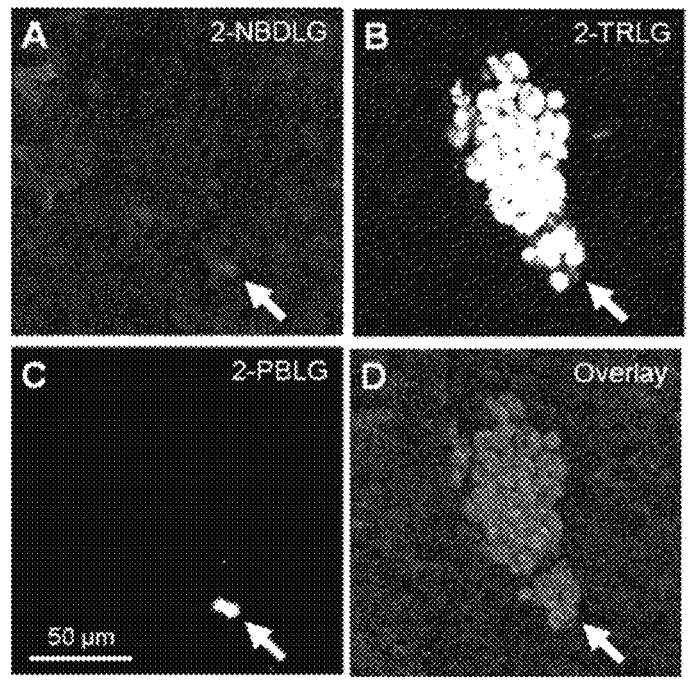
FIGS. 13A-13D are enlarged images of regions around the center of the cancer cell cluster shown FIGS. 9A-9E.

FIG. 12 is an image at a time point of 12 minutes after completion of administration of a mixed solution. Only cells indicated by an arrow emit blue fluorescence by 2-PBLG continuously and discriminated from other cells, suggesting that 2-PBLG is linked to these cells strongly (B, E). FIG. 13 is an image enlarging parts around the center of the cancer cell cluster shown in FIG. 11. Cells indicated by an arrow are visualized strongly by 2-PBLG. The arrow indicates 2-PBLG strongly positive cells. These cells show also intense green fluorescence by 2-NBDLG (A), however, it is difficult to discriminate these cells only by 2-NBDLG.

Example 8: Imaging Using 2-PBLG of a Tumor Cell Cluster Composed of Mouse Insulinoma Cells (MIN6) (Use of 2-PBLG/2-TRLG)

In the same manner as in Example 7, a mixed solution of 2-PBLG/2-TRLG was used instead of the mixed solution of 2-PBLG/2-NBDLG/2-TRLG.

Figure 14:
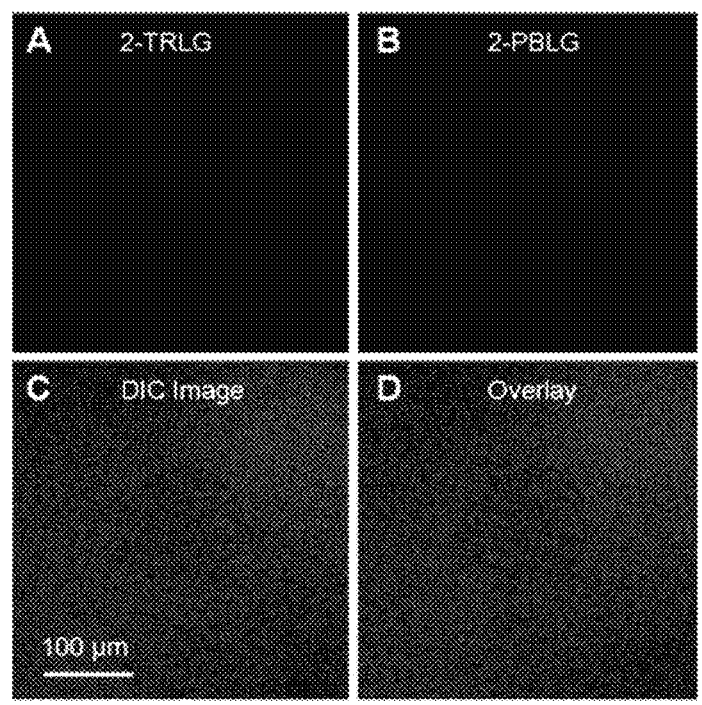
FIGS. 14A-14D are images acquired by a real time laser scanning confocal microscope before administration of a mixed solution composed of 100 µM of 2-PBLG and 20 µM of 2-TRLG to a tumor cell cluster composed of mouse insulinoma cells (MIN6) in Example 8.

FIG. 14 is an image before administration of a fluorescently labeled glucose derivative of a MIN6 cell cluster on day 13 of culture. A and B are fluorescence acquisition images in the wavelength regions of 580-740 nm (red) and 415-580 nm (blue), respectively. C is a differential interference micrograph. D is an overlaid image of them.

Figure 15:
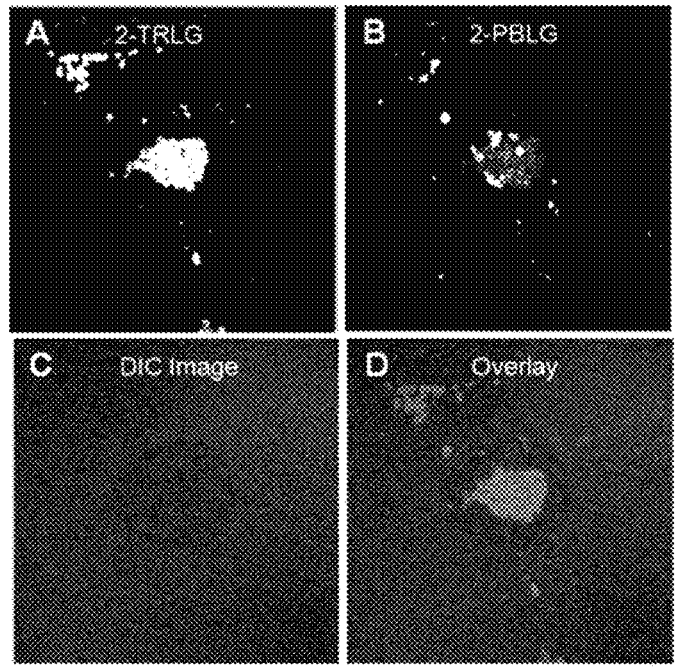
FIGS. 15A-15D are images acquired 2 minutes after completion of administration in Example 8.

FIG. 15 is an image at a time point of 2 minutes after initiation of washout after administering a fluorescence mixed solution containing 20 μM of 2-TRLG and 100 μM of 2-PBLG to a MIN 6 cell cluster for 5 minutes. When A is observed, it is found that plasma membrane-impermeable 2-TRLG invades into the cell having increased membrane permeability mainly present at the center of a cell cluster. At this time point, also parts of debris of cell tissue present on the outer edge of a cell cluster and outside of a cell cluster are stained. When B is observed, it is found that 2-PBLG invades once into the cell having increased membrane permeability as well. However, it is understood that, at this time point, 2-PBLG already starts to flow out from the inside of the cell, and the fluorescence intensity at the center of a cell cluster starts to weaken. It is to be noted that extremely intense blue fluorescence is emitted from some cells, among them. In the case of simultaneous administration of also 2-NBDLG when 2-PBLG and 2-TRLG are administered like in Example 7, 2-NBDLG and 2-TRLG were excited by 488 nm argon laser, then, 2-PBLG was excited by 405 nm diode laser. In this case, since the maximum fluorescence of 2-PBLG overlaps the excitation wavelength of 2-NBDLG, it is also supposed that the fluorescence signal of 2-PBLG weakens due to FRET effect depending on the local concentration. Further, increased fluorescence intensity in a region of 580 nm or more (skirt at longer wavelength side) of 2-NBDLG mixes in the fluorescence intensity distribution of 580-740 nm of 2-TRLG excited at 488 nm. In contrast, when a mixed solution of 2-PBLG/2-TRLG is used, both the FRET effect and the influence by the skirt at the longer wavelength side can be avoided, thus, it becomes possible to separate increased fluorescence intensity, leading to an advantage in quantification.

Figure 16:
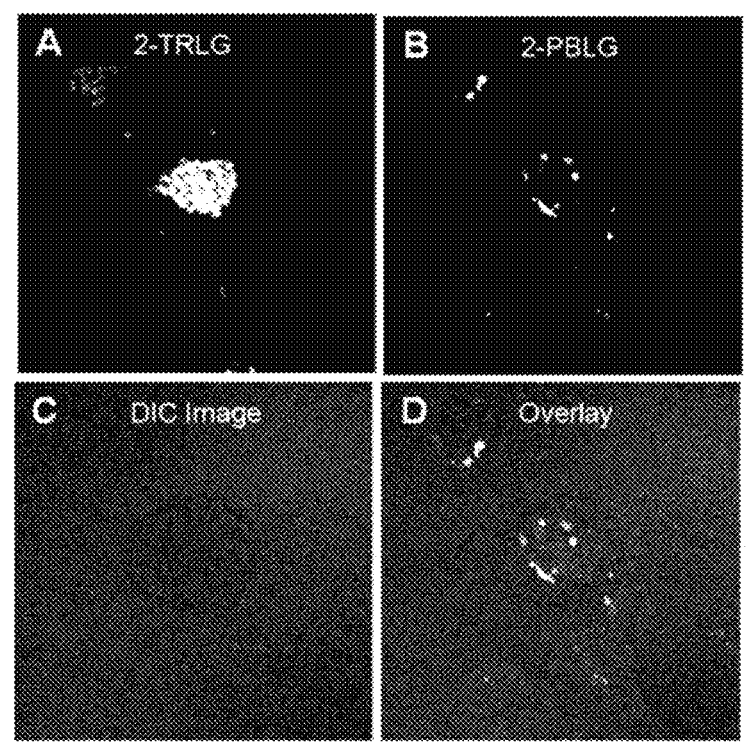
FIGS. 16A-16D are images acquired 8 minutes after completion of administration in Example 8.

FIG. 16 is equivalent to FIG. 15, excepting that FIG. 16 is an image 8 minutes after initiation of washout after completion of administration. 2-TRLG generating red color and 2-PBLG generating blue color provide much different distribution patterns (A, B, C), and it is difficult to explain the distribution of cells strongly positive for 2-PBLG by the increase in membrane permeability. Blue cells positive for 2-PBLG are scattered around the outer edge of the center of a cell cluster and the like (B, D). At a time point of 2 minutes after completion of administration, red fluorescence observed on the outer edge of cells is attenuated by washout.

Figure 17:
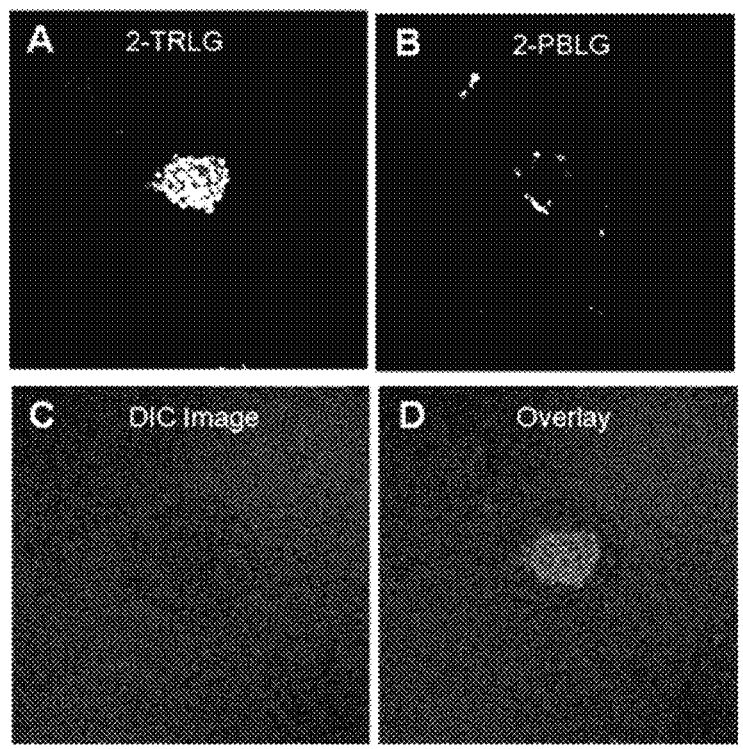
FIGS. 17A-17D are images acquired 12 minutes after completion of administration in Example 8.

FIG. 17 is equivalent to FIG. 16, excepting that FIG. 17 is an image 12 minutes after initiation of washout after completion of administration. There are still multiple cells showing the strongly positive signal of 2-PBLG (B, D).

The above-described detailed descriptions simply explain the objects and subjects of the present invention, and do not limit the scope of the appended claims. Various alterations and substitutions for the described embodiments, without departing from the scope of the appended claims, are apparent for those skilled in the art on the basis of teachings described in the present specification.

INDUSTRIAL APPLICABILITY

The present invention provides a novel fluorescently labeled sugar derivative emitting blue fluorescence color. Further, the present invention provides a new method for detecting tumor cells.

The invention claimed is:

1. A method for detecting a cancer cell, comprising the following steps:
    (a) detecting the fluorescence of a target cell, wherein the target cell is a cell present in tissue isolated from a living body or is a cell present in tissue of a living body;
    (b) a step of contacting the target cell with a composition containing a fluorescently labeled L-glucose derivative in which 3-carboxy-6,8-difluoro-7-hydroxycoumarin or 3-carboxymethyl-6,8-difluoro-7-hydroxy-4-methylcoumarin is linked as a fluorescent molecular group to the L-glucose, and
    (c) a step of detecting the fluorescence of the L-glucose derivative present in the target cell, wherein an increase in the fluorescence intensity in comparison with the fluorescence intensity of the target cell before said contacting step indicates that the target cell is a cancer cell.

2. The detection method according to claim 1, wherein the fluorescently labeled L-glucose derivative is a molecule in which 3-carboxy-6,8-difluoro-7-hydroxycoumarin or 3-carboxymethyl-6,8-difluoro-7-hydroxy-4-methylcoumarin as a fluorescent molecular group is linked to the 1-position, 2-position, 3-position, 4-position or 6-position of L-glucose via a —NH— bond.

3. The detection method according to claim 1, wherein the fluorescently labeled L-glucose derivative is 2-deoxy-2-((6, 8-difluoro-7-hydroxycoumarin-3-yl)carboxamido)-L-glucose or 2-deoxy-2-(2-(6,8-difluoro-7-hydroxy-4-methylcoumarin-3-yl)acetamido)-L-glucose.

4. The detection method according to claim 3, wherein the composition in the step (a) further contains 2-amino-2-deoxy-L-glucose to which sulforhodamine is linked to the 2-position of the 2-amino-2-deoxy-L-glucose via a sulfonamide linkage to form a fluorescently labeled sulforhodamine L-glucose derivative and the step (c) detects fluorescence of the fluorescently labeled L-glucose derivatives present in the target cell.

5. A composition for imaging target cells or target intracellular molecules comprising a fluorescently labeled sugar derivative, wherein the target cells are cancer cells and are cells present in tissue isolated from a living body or are cells present in tissue of a living body, and the fluorescently labeled sugar derivative is a fluorescently labeled L-glucose derivative in which 3-carboxy-6,8-difluoro-7-hydroxycoumarin or 3-carboxymethyl-6,8-difluoro-7-hydroxy-4-methylcoumarin as a fluorescent molecular group is linked.

6. The composition according to claim 5, wherein the fluorescently labeled L-glucose derivative is 2-deoxy-2-((6,8-difluoro-7-hydroxycoumarin-3-yl)carboxamido)-L-glucose or 2-deoxy-2-(2-(6,8-difluoro-7-hydroxy-4-methylcoumarin-3-yl)acetamido)-L-glucose.

7. The composition according to claim 5, wherein the composition further contains 2-amino-2-deoxy-L-glucose to which sulforhodamine is linked to the 2-position thereof via sulfonamide linkage.

8. A composition consisting of a fluorescently labeled sugar derivative, which is 2-deoxy-2-((6,8-difluoro-7-hydroxycoumarin-3-yl)carboxamido)-L-glucose or 2-deoxy-2-(2-(6,8-difluoro-7-hydroxy-4-methylcoumarin-3-yl)acetamido)-L-glucose.

9. A method of diagnosing cancer in a subject, the method comprising:
   (a) administering to the subject a composition containing a fluorescently labeled L-glucose derivative in which 3-carboxy-6,8-difluoro-7-hydroxycoumarin or 3-carboxymethyl-6,8-difluoro-7-hydroxy-4-methylcoumarin is linked as a fluorescent molecular group to the L-glucose; and
   (b) imaging said subject having received the L-glucose derivative in step (a) and detecting fluorescence of the L-glucose derivative in cancer cells of said subject.

10. A method of diagnosing cancer in a subject, the method comprising:
   (a) obtaining a biopsy sample from said subject;
   (b) contacting said biopsy sample with a composition containing a fluorescently labeled L-glucose derivative in which 3-carboxy-6,8-difluoro-7-hydroxycoumarin or 3-carboxymethyl-6,8-difluoro-7-hydroxy-4-methylcoumarin is linked as a fluorescent molecular group to the L-glucose; and
   (b) imaging said biopsy sample having been contacted with the L-glucose derivative in step (a) and detecting fluorescence of the L-glucose derivative in cancer cells in said biopsy sample.

* * * * *